(12) United States Patent
Tisdale et al.

(10) Patent No.: US 10,172,917 B2
(45) Date of Patent: Jan. 8, 2019

(54) TARGETED OESOPHAGEAL ADMINISTRATION OF ZN-$\alpha_2$-GLYCOPROTEINS (ZAG), METHODS AND FORMULATIONS THEREOF

(71) Applicant: ASTON UNIVERSITY, Birmingham (GB)

(72) Inventors: Michael Tisdale, Claverdon (GB); Steven Russell, Wednesbury (GB)

(73) Assignee: Aston University, Birmingham (GB)

( * ) Notice: Subject to any disclaimer, the term of this patent is extended or adjusted under 35 U.S.C. 154(b) by 0 days.

(21) Appl. No.: 15/175,579

(22) Filed: Jun. 7, 2016

(65) Prior Publication Data

US 2016/0346351 A1 Dec. 1, 2016

Related U.S. Application Data

(63) Continuation of application No. 14/418,912, filed as application No. PCT/GB2013/052039 on Jul. 31, 2013, now abandoned.

(60) Provisional application No. 61/677,984, filed on Jul. 31, 2012.

(51) Int. Cl.
| | |
|---|---|
| *A61K 38/00* | (2006.01) |
| *A61K 38/28* | (2006.01) |
| *A61K 38/17* | (2006.01) |
| *A61K 45/06* | (2006.01) |
| *A61K 9/00* | (2006.01) |
| *A61K 31/138* | (2006.01) |
| *A61K 47/56* | (2017.01) |

(52) U.S. Cl.
CPC ........ *A61K 38/1741* (2013.01); *A61K 9/0053* (2013.01); *A61K 31/138* (2013.01); *A61K 38/1709* (2013.01); *A61K 45/06* (2013.01); *A61K 47/56* (2017.08)

(58) Field of Classification Search
None
See application file for complete search history.

(56) References Cited

U.S. PATENT DOCUMENTS

| | | | | |
|---|---|---|---|---|
| 6,890,899 B1 * | 5/2005 | Tisdale | ............ | C07K 14/47 514/20.9 |
| 2003/0236190 A1 * | 12/2003 | Pillutla | ............ | C07K 14/65 514/6.7 |
| 2005/0148763 A1 * | 7/2005 | Sekimori | ............ | A61K 38/29 530/399 |

FOREIGN PATENT DOCUMENTS

WO    WO 2011/161427 A2    12/2011

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al (2001. J. Biol Chem. 276:49213-49220.*
de Boer et al., "The β-Adrenoceptors Mediating Relaxation of Rat Oesophageal Muscularis Mucosae are Predominantly of the β3-, but also of the β2-Subtype," Br. J. Pharmacol. (1993), 110:442-446, Macmillan Press Ltd.
Russell et al., "Role of Beta-Adrenergic Receptors in the Anti-Obesity and Anti-Diabetic Effects of Zinc-alpha2-Glycoprotein (ZAG)," Biochim. Biophys. Acta (2012), 1821(4):590-599.

* cited by examiner

*Primary Examiner* — Shulamith H Shafer
(74) *Attorney, Agent, or Firm* — Wagenknecht IP Law Group PC

(57) ABSTRACT

The invention provides formulations and methods for ameliorating symptoms associated with metabolic disorders, such as hypoglycemia, obesity, diabetes, and the like by targeted administration to the oesphagus of a subject of Zn-$\alpha_2$-glycoproteins or a functional fragment thereof, alone or in combination with additional agents, such as β adrenergin receptor agonists, β adrenergin receptor antagonists, and/or glycemic control agents.

14 Claims, 23 Drawing Sheets

Specification includes a Sequence Listing.

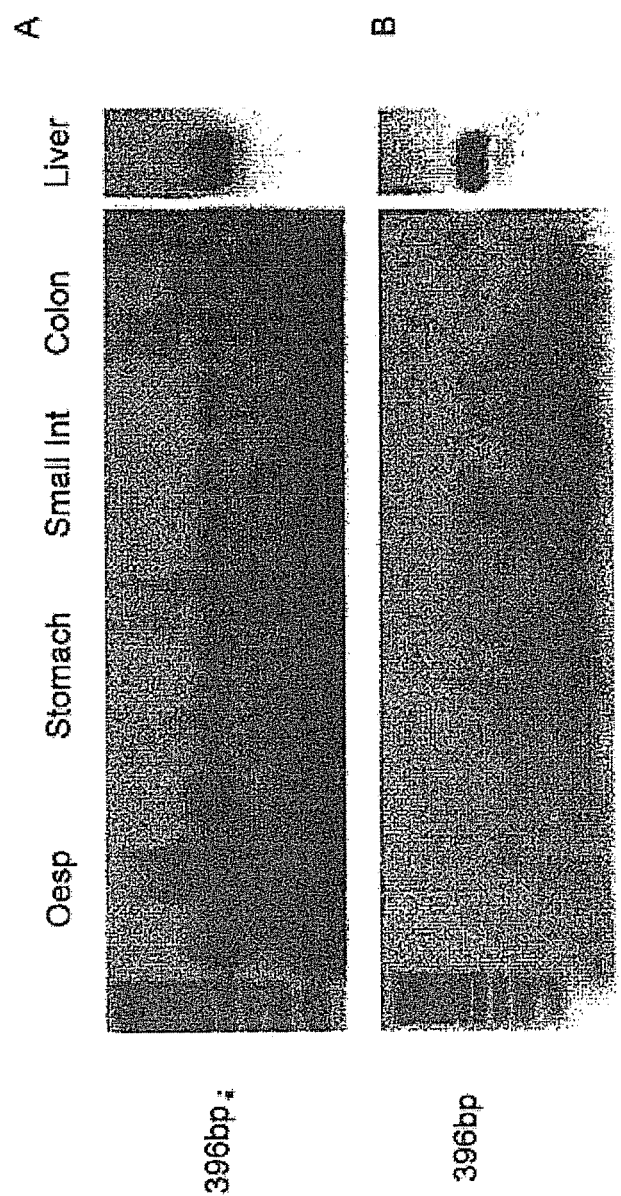
FIGSs. 6A - 6B

Gln Glu Asn Gln Asp Gly Arg Tyr Ser Leu Thr
Tyr Ile Tyr Thr Gly Leu Ser Lys His Val Glu
Asp Val Pro Ala Phe Gln Ala Leu Gly Ser Leu
Asn Asp Leu Gln Phe Phe Arg Tyr Asn Ser Lys
Asp Arg Lys Ser Gln Pro Met Gly Leu Trp Arg
Gln Val Glu Gly Met Glu Asp Trp Lys Glu Asp
Ser Gln Leu Gln Lys Ala Arg Glu Asp Met Glu
Thr Leu Lys Asp Ile Val Glu Tyr Tyr Asn Asp
Ser Asn Gly Ser His Val Leu Gln Gly Arg Phe
Gly Cys Glu Ile Glu Asn Asn Arg Ser Ser Gly
Ala Phe Trp Lys Tyr Tyr Tyr Asp Gly Lys Asp
Tyr Ile Glu Phe Asn Lys Glu Ile Pro Ala Trp
Val Pro Phe Asp Pro Ala Ala Gln Ile Thr Lys
Gln Lys Trp Glu Ala Glu Pro Val Tyr Val Gln
Arg Ala Lys Ala Tyr Leu Glu Glu Glu Cys Pro
Ala Thr Leu Arg Lys Tyr Leu Lys Tyr Ser Lys
Asn Ile Leu Asp Arg Gln Asp Pro Pro Ser Val
Val Val Thr Ser His Gln Ala Pro Gly Glu Lys
Lys Lys Leu Lys Cys Leu Ala Tyr Asp Phe Tyr
Pro Gly Lys Ile Asp Val His Trp Thr Arg Ala
Gly Gln Val Gln Glu Pro Glu Leu Arg Gly Asp
Val Leu His Asn Gly Asn Gly Thr Tyr Gln Ser
Trp Val Val Ala Val Pro Pro Gln Asp Thr
Ala Pro Tyr Ser Cys His Val Gln His Ser Ser
Leu Ala Gln Pro Leu Val Val Pro Trp Glu Ala
Ser COOH

FIG. 7

TARGETED OESOPHAGEAL ADMINISTRATION OF ZN-α₂-GLYCOPROTEINS (ZAG), METHODS AND FORMULATIONS THEREOF

CROSS REFERENCE TO RELATED APPLICATION(S)

This application is a continuation of U.S. application Ser. No. 14/418,912, filed Jan. 30, 2015, currently pending; based on PCT/GB2013/052039, filed Jul. 31, 2013; which claims the benefit of priority under 35 U.S.C. § 119(e) of U.S. Ser. No. 61/677,984, filed Jul. 31, 2012, the entire content of each of which is incorporated herein by reference.

BACKGROUND OF THE INVENTION

Field of the Invention

The present invention relates generally to medicinal formulations, and more particularly, to formulations and methods for altering the metabolism of a subject, as well as ameliorating disorders such as obesity, diabetes and insulin resistance.

Background Information

The prevalence of obesity in adults, children and adolescents has increased rapidly over the past 30 years in the United States and globally and continues to rise. Obesity is classically defined based on the percentage of body fat or, more recently, the body mass index (BMI), also called Quetlet index (National Task Force on the Prevention and Treatment of Obesity, Arch. Intern. Med., 160: 898-904 (2000); Khaodhiar, L. et al., Clin. Cornerstone, 2: 17-31 (1999)). The BMI is defined as the ratio of weight (kg) divided by height (in meters) squared.

Overweight and obesity are associated with increasing the risk of developing many chronic diseases of aging seen in the U.S. Such co-morbidities include type 2 diabetes mellitus, hypertension, coronary heart diseases and dyslipidemia, gallstones and cholecystectomy, osteoarthritis, cancer (of the breast, colon, endometrial, prostate, and gallbladder), and sleep apnea. It is estimated that there are around 325,000 deaths annually that are attributable to obesity. The key to reducing the severity of the diseases is to lose weight effectively. Although about 30 to 40% claim to be trying to lose weight or maintain lost weight, current therapies appear not to be working. Besides dietary manipulation, pharmacological management and in extreme cases, surgery, are sanctioned adjunctive therapies to treat overweight and obese patients (Expert Panel, National Institute of Health, Heart, Lung, and Blood Institute, 1-42 (June 1998); Bray, G. A., Contemporary Diagnosis and Management of Obesity, 246-273 (1998)). Drugs have side effects, and surgery, although effective, is a drastic measure and reserved for morbidly obese.

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction.

There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions. Increasing scrutiny is being given to the role of insulin resistance to the genesis, progression, and therapeutic management of this type of diabetic disease.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary defects of insulin resistance and islet failure with fewer or milder side effects than existing drugs.

ZAG has previously been investigated as a treatment for obesity and type 2 diabetes. ZAG is a soluble protein of Mr41kDa, which resembles a class 1 major histocompatability complex (MHC) heavy chain, and has a major groove capable of binding hydrophobic molecules, that could be important in its action. ZAG was first identified as the lipid mobilising factor in cancer cachexia following its isolation from the cachexia-inducing MAC16 tumour, and from the urine of cachectic patients. Treatment of either aged, or obese mice with ZAG produced a time-dependent decrease in body weight through specific loss of carcass lipid, while there was an expansion of the non-fat carcass mass. ZAG is produced by a range of tissues including white (WAT) and brown (BAT) adipose tissue, liver, heart, lung and skeletal muscle, as well as certain tumours that induce cachexia. Expression of ZAG mRNA in adipose tissue is high in cancer cachexia, where lipid stores are low, and low in obesity, where lipid stores are high. Thus ZAG expression is negatively correlated with BMI and fat mass. ZAG expression is negatively regulated by tumour necrosis factor-α (TNF-α), and positively regulated by the PPARγ agonist rosiglitazone, β3-adrenergic receptor (β3-AR) agonists and glucocorticoids. ZAG also induces its own expression in adipose tissue through interaction with a β3-AR. In this way extracellular ZAG can induce expression of intracellular ZAG in target tissues, which has been suggested to be more important locally than circulating ZAG.

Previously studies have administration ZAG by either the i.p., or i.v. routes. However, neither route is convenient for clinical use. There remains a lack of effective and safe alternatives for altering metabolism and treatment of metabolic diseases, such as obesity and diabetes. There is therefore a need for new formulations for such uses which provide spefic targeting of therapeutics.

SUMMARY OF THE INVENTION

The present invention is based in part on the finding that ZAG has the ability to induce its own expression through binding β3-ARs present in the oesophagus thereby enabling activation of the therapeutic effect of ZAG before being digested in lower regions of the gastrointestinal tract. Such a finding is useful in methods of targeting the oesophagus for moderating body weight, improving insulin responsiveness or ameliorating the symptoms associated with diabetes.

In one embodiment the present invention provides a formulation including zinc-$\alpha_2$-glycoprotein (ZAG), a ZAG variant, a modified ZAG, or a functional fragment thereof, wherein the formulation is formulated to specifically target β3-adrenergic receptors (β3-ARs) of the oesophagus to increase specific binding of ZAG, the ZAG variant, the modified ZAG, or the functional fragment thereof with a β3-adrenergic receptor (β3-AR) of the oesophagus thereby providing targeted delivery of the formulation to the oesophagus.

In another embodiment, the invention provides a method of delivering a therapeutic agent to a subject. The method includes targeting the therapeutic agent to a receptor in the oesophagus of the subject, wherein the therapeutic agent is zinc-$\alpha_2$-glycoprotein (ZAG), a ZAG variant, a modified ZAG, or a functional fragment thereof formulated to specifically target the receptor to increase specific binding of the therapeutic agent to the receptor, and wherein the receptor is a β3-adrenergic receptor (β3-AR), thereby delivering the therapeutic agent to the subject.

In another embodiment, the invention provides a method for delivering a zinc-$\alpha_2$-glycoprotein (ZAG) to a mammalian subject, the method including administering to the oesophagus of the subject the formulation as described herein.

In another embodiment, the invention provides a method for increasing a subject's endogenous level of a zinc-$\alpha_2$-glycoprotein (ZAG), the method including administering to the oesophagus of the subject the formulation as described herein.

In a further aspect, the present invention provides a method of ameliorating symptoms of diabetes or obesity in a mammalian subject. The method includes administering to the oesophagus of the subject a therapeutically effective dosage of a formulation as described herein. In one embodiment, the formulation may be administered in combination with a glycemic reducing agent selected from insulin, glucagon-like peptide-1 (GLP-1), or analogs thereof in any sequence or simultaneously.

BRIEF DESCRIPTION OF THE DRAWINGS

FIG. 4A shows expression of murine ZAG in serum of ob/ob mice administered human ZAG or PBS orally for 8 days as shown in FIG. 1. Each lane is a sample from an individual mouse. The blot was probed with anti-mouse ZAG antibody. FIG. 4B shows human ZAG was electrophoretically blotted, and probed with antibodies specific to human and mouse ZAG. FIG. 4C shows expression of ZAG in WAT quantitated using an anti-mouse ZAG antibody after 8 days treatment with human ZAG Differences from PBS treated animals are shown as ***, p<0.001.

FIG. 5A is a graphical representation showing glucose uptake into epididymal (ep), subcutaneous (sc) and visceral (vis) adipocytes from animals treated with PBS and ZAG with or without propanolol (Prop) for 8 days in the absence (closed bars), or presence (open bars) of insulin (10 nM).

FIG. 5B is a graphical representation showing glucose uptake into brown adipocytes from mice treated with PBS, ZAG or ZAG+propanolol for 8 days with or without insulin (10 nM).

FIG. 5C is a graphical representation showing glucose uptake into isolated gastrocnemius muscle of ob/ob mice administered either PBS or ZAG with or without propanolol for 8 days.

FIG. 5D is a pictorial representation showing quantitation of serum ZAG in mice treated with PBS, ZAG or ZAG+ propanolol for 3 days by immunoblotting using an anti-mouse ZAG monoclonal antibody. Each lane represents serum from an individual mouse. Differences from PBS treated animals are shown as *, $p<0.05$ or ***, $P<0.001$, while differences from ZAG treated animals are shown as ##, $p<0.001$.

FIGS. 6A-6C are a series of pictorial representations showing ZAG gene expression in mouse tissues examined by RT-PCR.

FIG. 6A shows tissue specificity of expression from mice treated with ZAG orally.

FIG. 6B shows ZAG expression in control mice.

FIG. 6C shows ZAG mRNA expression in mouse tissue after either oral administration of ZAG (■) or PBS (□). Differences from PBS treated animals are shown as ***, $P<0.001$.

FIG. 7 is a pictorial diagram showing the complete amino acid sequence (SEQ ID NO: 1) of the human plasma Zn-$\alpha_2$-glycoprotein, as published by T. Araki et al. (1988) "Complete amino acid sequence of human plasma Zn-$\alpha_2$-glycoprotein and its homology to histocompatibility antigens."

DETAILED DESCRIPTION OF THE INVENTION

Figure 1A:
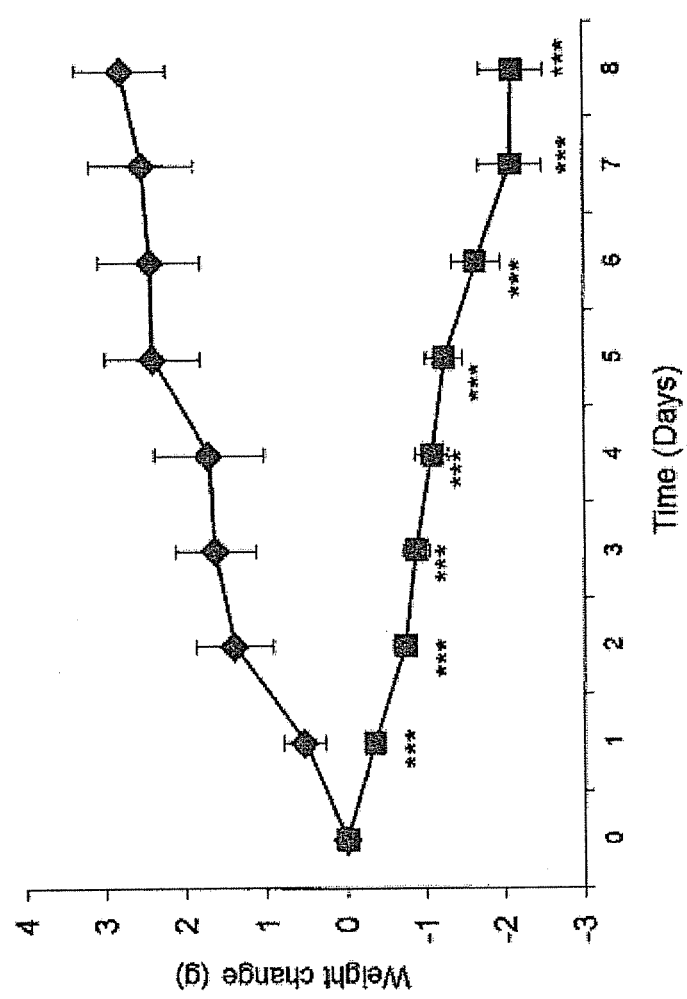
FIGS. 1A-1C are graphical diagrams showing the effect of human ZAG on body weight (A), rectal temperature (B) and urinary glucose excretion (C) in ob/ob mice. ZAG was dissolved in the drinking water so that animals consumed 50 μgday$^{-1}$ (■), while a control group received an equal volume of PBS (♦) (0.5 ml in 5 ml water). Differences from PBS controls are shown as ***, p<0.001.

The present invention is based on the observation that Zinc-$\alpha_2$-glycoprotein (ZAG) binds β3-AR in the oesophagus to induce its own expression, as opposed to being degraded in the lower regions of the gastrointestinal tract. As such, the invention provides methods and formulation for targeted delivery of ZAG to β3-AR receptors of the oesophagus to treat a variety of disorders.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The complete amino acid sequence of ZAG has been reported in a paper entitled "Complete amino acid sequence of human plasma Zinc-$\alpha_2$-glycoprotein and its homology to histocompatibility antigens" by T. Araki et al. (1988) Proc. Natl. Acad. Sci. USA., 85, 679-683, wherein the glycoprotein was shown as consisting of a single polypeptide chain of 276 amino acid residues having three distinct domain structures (A, B and C) and including two disulfide bonds together with N-linked glycans at three glycosylation sites. This amino acid sequence of the polypeptide component is set out in FIG. 10 of the accompanying drawings. Although some subsequent publications have indicated that the composition of human ZAG can vary somewhat when isolated from different body fluids or tissues, all preparations of this material have substantially the same immunological characteristics. As reported by H. Ueyama, et al. (1991) "Cloning and nucleotide sequence of a human Zinc-$\alpha_2$-glycoprotein cDNA and chromosomal assignment of its gene", Biochem. Biophys. Res. Commun. 177, 696-703, cDNA of ZAG has been isolated from human liver and prostate gland libraries, and also the gene has been isolated, as reported by Ueyama et al., (1993) "Molecular cloning and chromosomal assignment of the gene for human Zinc-$\alpha_2$-glycoprotein", Biochemistry 32, 12968-12976. H. Ueyama et al. have also described, in J. Biochem. (1994) 116, 677-681, studies on ZAG cDNAs from rat and mouse liver which, together with the glycoprotein expressed by the corresponding mRNAs, have been sequenced and compared with the human material. Although detail differences were found as would be expected from different species, a high degree of amino acid sequence homology was found with over 50% identity with the human counterpart (over 70% identity within domain B of the glycoprotein). Again, common immunological properties between the human, rat and mouse ZAG have been observed.

The purified ZAG discussed above was prepared from fresh human plasma substantially according to the method described by Ohkubo et al. (Ohkubo et al. (1988) "Purification and characterisation of human plasma Zn-$\alpha_2$-glycoprotein" Prep. Biochem., 18, 413-430). It will be appreciated that in some cases fragments of the isolated lipid mobilizing factor, of ZAG, or of anti-ZAG antibodies may be produced without loss of activity, and various additions, deletions or substitutions may be made which also will not substantially affect this activity. As such, the methods of the invention also include use of functional fragments of anti-ZAG antibodies. The antibody or fragment thereof used in these therapeutic applications may further be produced by recombinant DNA techniques such as are well known in the art based possibly on the known cDNA sequence for Zn-$\alpha_2$-glycoprotein which has been published for example in H. Ueyama et al. (1994) "Structure and Expression of Rat and Mouse mRNAs for Zn-$\alpha_2$-glycoprotein" J. Biochem., 116, 677-681. In addition, the antibody or fragment thereof used in these therapeutic applications may further include post-expression modifications of the polypeptide, for example, glycosylations, acetylations, phosphorylations and the like, as well as other modifications known in the art, both naturally occurring and non-naturally occurring.

As used herein, ZAG polypeptides or proteins include variants of wild type proteins which retain their biological function. As such, one or more of the residues of a ZAG protein can be altered to yield a variant or truncated protein, so long as the variant retains it native biological activity. Conservative amino acid substitutions include, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. However, the invention also envisions variants with non-conservative substitutions.

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

As discussed above, the present invention includes use of a function fragment of a ZAG polypeptide or protein. A functional fragment, is characterized, in part, by having or affecting an activity associated with weight loss, lowering blood glucose level, increasing body temperature, improving glucose tissue uptake, increasing expression of Bet3 receptors, increasing expression of ZAG, increasing expression of Glut 4, and/or increasing expression of UCP 1 and UCP 3. Thus, the term "functional fragment," when used herein refers to a polypeptide that retains one or more biological functions of ZAG. Methods for identifying such a functional fragment of a ZAG polypeptide, are generally known in the art.

ZAG and/or fragments thereof has been previously shown to bring about a weight reduction or reduction in obesity in mammals, as, disclosed in U.S. Pat. Nos. 6,890,899 and 7,550,429, and in U.S. Pub. No. 2010/0173829, the entire contents of each of which is incorporated herein by reference. In one embodiment, the present invention demonstrates that anti-ZAG antibodies and/or functional fragments thereof reduces weight loss in models of cachexia. It is therefore contemplated that the methods of the instant invention provide a detectable effect on symptoms associated with cachexia and/or diseases associated with muscle wasting disease.

Accordingly, in one aspect, the invention provides a method of ameliorating the symptoms of insulin resistance, obesity or diabetes in a subject. The method includes administering to the subject in need of such treatment a therapeutically effective dosage of an inhibitor of the biological activity of a polypeptide having the sequence as shown in SEQ ID NO: 1. In one embodiment, the treatment regimen may be for months (e.g., 1, 2, 3, 4, 5, 6, 7, 8, 9, 10, 11, or 12 months), or years. In another embodiment, the polypeptide is administered for a period of up to 21 days or longer. In another embodiment, the amelioration of symptoms is detectable within days (e.g., 1, 2, 3, 4, 5, 6, or 7 days), weeks (e.g., 1, 2, 3, or 4 weeks), or months (e.g., 1, 2, 3, 4, 5, 6, 7, 8, 9, 10, 11, or 12 months) of initiating treatment. In another embodiment, the treatment regimen is about 10 days wherein there is amelioration of symptoms following treatment. In another embodiment, the treatment regimen is about 21 days wherein there is amelioration of symptoms following treatment.

In addition, it has been observed that a lipid mobilizing agent having similar characteristics of ZAG and/or fragments thereof has also been used to bring about a weight reduction or reduction in obesity in mammals, as disclosed in U.S. Published App. No. 2006/0160723, incorporated by herein by reference in its entirety. Finally, it has been shown that ZAG and/or functional fragments thereof increases the insulin responsiveness of adipocytes and skeletal muscle, and produces an increase in muscle mass through an increase in protein synthesis coupled with a decrease in protein degradation regardless of whether a weight reduction or reduction in obesity is observed during treatment (see U.S. Ser. No. 12/614,289, incorporated herein by reference).

Additionally, β3 agonists are reportedly effective insulin sensitizing agents in rodents and their potential to reduce blood glucose levels in humans has been a subject of investigation. Activation of β3 agonists adrenoceptors stimulates fat oxidation, thereby lowering intracellular concentrations of metabolites including fatty acyl CoA and diacylglycerol, which modulate insulin signaling. Furthermore, it is contemplated herein that certain β3 receptor agonists may not have found success in clinical trials given that one category of β3 receptors available to these agents is located in the digestive system and particularly in the mouth, pharynx, esophagus and stomach, resulting in minimal, if any, exposure of the agonist to most of these receptors. This theory is supported by the observation that several of the β3 agonist therapeutic agents were found to be efficacious but had limited bioavailability in the plasma space.

A number of formulations are provided herein for specifically targeting β3-ARs of the oesphagus. A formulation can be in any form which facilitates increased binding of ZAG with β3-ARs of the oesophagus, e.g., liquid, gel, suspension, or emulsion. A formulation typically will include one or more compositions that have been purified, isolated, or extracted (e.g., from plants) or synthesized.

Any of the formulations can be prepared using well known methods by those having ordinary skill in the art, e.g., by mixing the recited ingredients in the proper amounts. Ingredients for inclusion in a formulation are generally commercially available.

In one embodiment the present invention provides a formulation including zinc-$\alpha_2$-glycoprotein (ZAG), a ZAG variant, a modified ZAG, or a functional fragment thereof, wherein the formulation is formulated to specifically target β3-adrenergic receptors (β3-ARs) of the oesophagus to increase specific binding of ZAG, the ZAG variant, the modified ZAG, or the functional fragment thereof with a β3-adrenergic receptor (β3-AR) of the oesophagus thereby providing targeted delivery of the formulation to the oesophagus. However, it should be understood that the ZAG may be derived from any source provided that the ZAG retains the activity of wild-type ZAG. In one embodiment, the further includes a pharmaceutically acceptable carrier, which constitutes one or more accessory ingredients.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The term "therapeutically effective amount" or "effective amount" means the amount of a compound or pharmaceutical composition that will elicit the biological or medical response of a tissue, system, animal or human that is being sought by the researcher, veterinarian, medical doctor or other clinician.

In some embodiments, the formulations of the invention are intended to be administered to the oesophagus daily. As used herein, the terms "administration" or "administering" are defined to include an act of providing a compound or pharmaceutical composition of the invention to a subject in need of treatment.

As used herein, the term "ameliorating" or "treating" means that the clinical signs and/or the symptoms associated with cachexia are lessened as a result of the actions performed.

As used herein, the terms "reduce" and "inhibit" are used together because it is recognized that, in some cases, a decrease can be reduced below the level of detection of a particular assay. As such, it may not always be clear whether the expression level or activity is "reduced" below a level of detection of an assay, or is completely "inhibited." Nevertheless, it will be clearly determinable, following a treatment according to the present methods, that amount of weight loss in a subject is at least reduced from the level prior to treatment.

ZAG has been attributed a number of biological roles, but its role as an adipokine regulating lipid mobilization and utilization is most important in regulating body composition. Previous studies suggested that the increase in protein synthesis was due to an increase in cyclic AMP through interaction with the β-adrenoreceptor, while the decrease in protein degradation was due to reduced activity of the ubiquitin-proteasome proteolytic pathway. Studies in db/db mice show that insulin resistance causes muscle wasting through an increased activity of the ubiquitin-proteasome pathway. An increased phosphorylation of both PKR and eIF2α will reduce protein synthesis by blocking translation initiation, while activation of PKR will increase protein degradation through activation of nuclear factor-κB (NF-κB), increasing expression of proteasome subunits. In vitro studies using myotubes in the presence of high extracellular glucose showed that activation of PKR led to activation of p38MAPK and formation of reactive oxygen species (ROS). p38MAPK can phosphorylate and activate cPLA$_2$ at Ser-505 causing release of arachidonic acid, a source of ROS. Hyperactivation of p38MAPK in skeletal muscle has been observed in models of diet-induced obesity. In addition caspase-3 activity has been shown to be increased in skeletal muscle of diabetic animals, which may be part of the signaling cascade, since it can cleave PKR leading to activation. Without being bound to theory, the ability of ZAG to attenuate these signaling pathways provides an explanation regarding its ability to increase muscle mass. As such, an anti-ZAG antibody is demonstrated to decrease loss of muscle mass in cachexia situations.

ZAG counters some of the metabolic features of the diabetic state including a reduction of plasma insulin levels and improved response in the glucose tolerance test. Thus, in another aspect, the invention provides a method of decreasing plasma insulin levels in a subject. The method includes administering to the oesophagus of a subject a therapeutically effective dosage of a polypeptide having the sequence as shown in SEQ ID NO: 1 or a fragment thereof. In one embodiment, the decrease in plasma insulin occurs within 3 days of initiating treatment. In another embodiment, the treatment regimen is administered for 10 days or longer. In another embodiment, the treatment regimen is administered for 21 days or longer.

In addition, ZAG has been shown to increase glucose oxidation and increase the tissue glucose metabolic rate in adult male mice. This increased utilization of glucose would explain the fall in both blood glucose and insulin levels in ob/ob mice administered ZAG. Triglyceride utilization was also increased in mice administered ZAG, which would explain the fall in plasma non-esterified fatty acids (NEFA) and triglycerides (TG) despite the increase in plasma glycerol, indicative of increased lipolysis. The increased utilization of lipid would be anticipated from the increased expression of UCP1 and UCP3 in BAT and UCP3 in skeletal muscle, resulting in an increase in body temperature. Thus, ZAG is identified as a lipid mobilizing factor capable of inducing lipolysis in white adipocytes of the mouse in a GTP-dependent process, similar to that induced by lipolytic hormones. As such, in one embodiment, amelioration of the symptoms associated with hyperglycemia also includes an increase in body temperature of about 0.5° C. to about 1° C. during treatment. In one embodiment, the increase in body temperature occurs within 4 days of initiating treatment. In another embodiment, amelioration of the symptoms associated with hyperglycemia also includes an increase in pancreatic insulin as compared to pancreatic insulin levels prior to treatment, since less insulin is needed to control blood glucose as a result of the presence of ZAG.

ZAG has also been shown to counter some of the metabolic features of the diabetic state including a reduction of plasma insulin levels and improved response in the glucose tolerance test. In addition ZAG increases the responsiveness of epididymal adipocytes to the lipolytic effect of a β3-adrenergic stimulant. ZAG also increases the expression of HSL and ATGL in epididymal adipose tissue which have been found to be reduced in the obese insulin-resistant state. Factors regulating the expression of HSL and ATGL are not known. However, the specific ERK inhibitor, PD98059 downregulated HSL expression in response to ZAG, suggesting a role for MAPK in this process. Mice lacking MAPK phosphatase-1 have increase activities of ERK and p38MAPK in WAT, and are resistant to diet-induced obesity due to enhanced energy expenditure. Previous studies have suggested a role for MAPK in the ZAG-induced expression of UCP3 in skeletal muscle. ERK activation may regulate lipolysis in adipocytes by phosphorylation of serine residues of HSL, such as Ser-600, one of the sites phosphorylated by protein kinase A.

ZAG administration to rats has also been shown to increase the expression of ATGL and HSL in the rat. ATGL may be important in excess fat storage in obesity, since ATGL knockout mice have large fat deposits and reduced NEFA release from WAT in response to isoproterenol, although they did display normal insulin sensitivity. In contrast HSL null mice, when fed a normal diet, had body weights similar to wild-type animals. However, expression of both ATGL and HSL are reduced in human WAT in the obese insulin-resistant state compared with the insulin sensitive state, and weight reduction also decreased mRNA and protein levels.

Stimulation of lipolysis alone would not deplete body fat stores, since without an energy sink the liberated NEFA would be resynthesised back into triglycerides in adipocytes. To reduce body fat, ZAG not only increases lipolysis, as shown by an increase in plasma glycerol, but also increases lipid utilization, as shown by the decrease in plasma levels of triglycerides and NEFA. This energy is channeled into heat, as evidenced by the 0.4° C. rise in body temperature in rats treated with ZAG. The increased energy utilization most likely arises from the increased expression of UCP1, which has been shown in both BAT and WAT after administration of ZAG. An increased expression of UCP1 would be expected to decrease plasma levels of NEFA, since they are the primary substrates for thermogenesis in BAT. BAT also has a high capacity for glucose utilization, which could partially explain the decrease in blood glucose. In addition there was increased expression of GLUT4 in skeletal muscle and WAT, which helps mediate the increase in glucose uptake in the presence of insulin. In mice treated with ZAG there was an increased glucose utilization/oxidation by brain, heart, BAT and gastrocnemius muscle, and increased production of $^{14}CO_2$ from D-[U-$^{14}$C] glucose, as well as [$^{14}$C carboxy] triolein. There was also a three-fold increase in oxygen uptake by BAT of ob/ob mice after ZAG administration.

While ZAG increased expression of HSL in epididymal adipocytes there was no increase in either subcutaneous or visceral adipocytes. A similar situation was observed with expression of adipose triglyceride lipase (ATGL). Expression of HSL and ATGL correlated with expression of the active (phospho) form of ERK. Expression of HSL and ATGL in epididymal adipocytes correlated with an increased lipolytic response to the β3 agonist, BRL37344. This result suggests that ZAG may act synergistically with β3 agonists, and suggests that anti-ZAG antibodies may act synergistically with β3 antagonists.

As used herein, the term "agonist" refers to an agent or analog that is capable of inducing a full or partial pharmacological response. For example, an agonist may bind productively to a receptor and mimic the physiological reaction thereto. As used herein, the term "antagonist" refers to an agent or analog that does not provoke a biological response itself upon binding to a receptor, but blocks or dampens agonist-mediated responses. The methods and formulations of the invention may include administering anti-ZAG antibodies, or a functional fragment thereof, in combination with a β3 antagonist, such as but not limited to BRL37344, or a β3 agonist.

Examples of β3 agonists that may be used in the present invention include, but are not limited to: epinephrine (adrenaline), norepinephrine (noradrenaline), isoprotenerol, isoprenaline, propranolol, alprenolol, arotinolol, bucindolol, carazolol, carteolol, clenbuterol, denopamine, fenoterol, nadolol, octopamine, oxyprenolol, pindolol, [(cyano)pindolol], salbuterol, salmeterol, teratolol, tecradine, trimetoquinolol, 3'-iodotrimetoquinolol, 3',5'-iodotrimetoquinolol, Amibegron, Solabegron, Nebivolol, AD-9677, AJ-9677, AZ-002, CGP-12177, CL-316243, CL-317413, BRL-37344, BRL-35135, BRL-26830, BRL-28410, BRL-33725, BRL-37344, BRL-35113, BMS-194449, BMS-196085, BMS-201620, BMS-210285, BMS-187257, BMS-187413, the CONH2 substitution of SO3H of BMS-187413, the racemates of BMS-181413, CGP-20712A, CGP-12177, CP-114271, CP-331679, CP-331684, CP-209129, FR-165914, FR-149175, ICI-118551, ICI-201651, ICI-198157, ICI-D7114, LY-377604, LY-368842, KTO-7924, LY-362884, LY-750355, LY-749372, LY-79771, LY-104119, L-771047, L-755507, L-749372, L-750355, L-760087, L-766892, L-746646, L-757793, L-770644, L-760081, L-796568, L-748328, L-748337, Ro-16-8714, Ro-40-2148, (−)-RO-363, SB-215691, SB-220648, SB-226552, SB-229432, SB-251023, SB-236923, SB-246982, SR-58894A, SR-58611, SR-58878, SR-59062, SM-11044, SM-350300, ZD-7114, ZD-2079, ZD-9969, ZM-215001, and ZM-215967.

Examples of β-AR antagonists that may be used in the present invention include, but are not limited to: propranolol, (−)-propranolol, (+)-propranolol, practolol, (−)-practolol, (+)-practolol, CGP-20712A, ICI-118551, (−)-bupranolol, acebutolol, atenolol, betaxolol, bisoprolol, esmolol, nebivolol, metoprolol, acebutolol, carteolol, penbutolol, pindolol, carvedilol, labetalol, levobunolol, metipranolol, nadolol, sotalol, and timolol.

Induction of lipolysis in rat adipocytes by ZAG is suggested to be mediated through a β3-AR, and the effect of ZAG on adipose tissue and lean body mass may also be due to its ability to stimulate the β3-AR. Induction of UCP1 expression by ZAG has been shown to be mediated through interaction with a β3-AR. The increased expression of UCP1 in WAT may also be a β3-AR effect through remodeling of brown adipocyte precursors, as occurs with the β3-AR agonist CL316,243. Using knock-out mice the antiobesity effect of β3-AR stimulation has been mainly attributed to UCP1 in BAT, and less to UCP2 and UCP3 through the UCP1-dependent degradation of NEFA released from WAT. Glucose uptake into peripheral tissues of animals is stimulated by cold-exposure, an effect also mediated through the β3-AR. However, targeting the β3-AR has been more difficult in humans than in rodents, since β3-AR play a less prominent role than β1 and β2-AR subtypes in the control of lipolysis and nutritive blood flow in human subcutaneous abdominal adipose tissue. However, despite this the β3-AR agonist CL316,243 has been shown to increase fat oxidation in healthy young male volunteers. This may be due to the ability of β-adrenergic agonists to increase the number of β3-AR in plasma membranes from BAT.

In one embodiment involving the treatment of obesity or diabetes in which it is desired to activate the β-3AR mechanism to achieve the desired lipolysis, glucose consumption, insulin sensitization, protein synthesis, increased energy expenditure, and the like. In this circumstance with some subjects it may be observed that the administered ZAG, or more likely the β-3AR agonist will exhibit some undesired activity at one or more of the β-1AR or the β-2AR, causing side effects or diminishment of desired efficacy. This circumstance would then call for the additional administration of β-AR antagonists, sometimes referred to as "classic beta blockers" so as to prevent the undesired activity at the β-1AR or β-2AR. These β-AR antagonists would preferably, but not necessarily, be selected to block the receptor subtype (one of β-1AR, β-2AR) that is associated with the side effect or mitigation of efficacy.

In another embodiment, involving treatment of lipidystrophy, in which fat masses are disproportionate to the normal distribution within a subject, and in which loss of fat mass is desired. In this case, the administration of one or more of ZAG, a β-3AR agonist and a β-AR antagonist would be desired, with reasoning similar to the first circumstance.

All methods may further include the step of bringing the active ingredient(s) into association with a pharmaceutically acceptable carrier, which constitutes one or more accessory ingredients. Pharmaceutically acceptable carriers useful for formulating a composition for administration to the oesophagus of a subject include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. In addition, such physiologically acceptable compounds may further be in salt form (i.e., balanced with a counter-ion such as $Ca^{2+}$, $Mg^{2+}$, $Na^+$, $NH_4^+$, etc.), provided that the carrier is compatible with the desired route of administration (e.g., bucal, oral, sublingual, etc.).

Formulations of the present invention may also include one or more excipients. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; and glycine or other amino acids. Buffer systems for use with the formulations include citrate; acetate; bicarbonate; and phosphate buffers.

Formulations of the present invention are formulated for specifically targeting the oesphagus of a subject. Such formulation may be presented as rapid-melt oral formulations, lozenges, or suspensions of the active compound in an aqueous liquid or non-aqueous liquid such as a syrup, an elixir, or an emulsion.

In one embodiment, the formulation includes about 1.0 mg to 1000 mg ZAG. In another embodiment, the formulation includes about 1.0 mg to about 500 mg ZAG. In another embodiment, the formulation includes about 1.0 mg to about 100 mg ZAG. In another embodiment, the formulation includes about 1.0 mg to about 50 mg ZAG. In another embodiment, the formulation includes about 1.0 mg to about 10 mg ZAG. In another embodiment, the formulation includes about 5.0 mg ZAG.

In one embodiment, the formulation of the present invention is administered directly to the oesophagus or to the oesophagus via oral, sublingual, bucal or intranasal routes. In such embodiments, the formulation is at least 70, 75, 80, 85, 90, 95 or 100% as effective as any other route of administration.

The total amount of formulation to be administered in practicing a method of the invention can be administered to a subject as a single dose, for example by bolus or ingestion over a relatively short period of time, or can be administered using a fractionated treatment protocol, in which multiple doses are administered over a prolonged period of time (e.g., once daily, twice daily, etc.). One skilled in the art would know that the amount of formulation depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

Accordingly, in certain embodiments, the methods of the invention include an intervalled treatment regimen. It was observed that long-term daily administration of ZAG in ob/ob mice results in continuous weight loss. As such, in one embodiment, the treatment of ZAG, alone or in combination with one or more β-AR antagonists or β3-AR agonists, is administered every other day. In another embodiment, the treatment is administered every two days. In another embodiment, the treatment is administered every three days. In another embodiment, the treatment is administered every four days.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Targeted Administration of Zinc-$\alpha_2$-Glycoprotein to the Oesophagus

In this example it is shown that targeted administration of human ZAG which is a 41 kDa protein, specifically to the oesophagus, as opposed to other regions of the gastrointestinal tract, of ob/ob mice at 50 μg day$^{-1}$po in drinking water produced a progressive loss of body weight (5 g after 8 days treatment), together with a 0.5° C. increase in rectal temperature, and a 40% reduction in urinary excretion of glucose. There was also a 33% reduction in the area under the curve during an oral glucose tolerance test and an increased sensitivity to insulin. These results were similar to those after iv administration of ZAG. However, tryptic digestion was shown to inactivate ZAG. There was no evidence of human ZAG in the serum, but a 2-fold elevation of murine ZAG, which was also observed in target tissues such as white adipose tissue. To determine whether the effect was due to interaction of the human ZAG with the β-adrenoreceptor (β-AR) in the gastrointestinal tract before digestion, ZAG was co-administered to ob/ob mice together with propanolol (40 mgkg$^{-1}$), a non-specific β-AR antagonist. The effect of ZAG on body weight, rectal temperature, urinary glucose excretion, improvement in glucose disposal and increased insulin sensitivity were attenuated by propanolol, as was the increase in murine ZAG in the serum. These results suggest that oral administration of ZAG increases serum levels through interaction with a β-AR in the upper gastrointestinal tract, and gene expression studies showed this to be specifically in the oesophagus.

The following materials and methods were utilized.

Materials—

FCS (foetal calf serum) was from Biosera (Sussex, UK), while DMEM (Dulbecco's modified Eagles Medium) was from PAA (Somerset, UK) and Freestyle medium was purchased from Invitrogen (Paisley, UK). Hybond A nitrocellulose membranes and peroxidise—conjugated rabbit anti-mouse antibody were from GE Healthcare (Bucks, UK), while enhanced chemiluminescene (ECL) development kits were purchased from Thermo Scientific (Northumberland, UK). Mouse monoclonal antibodies to full-length human and mouse ZAG were from Santa Cruz Biotechnology (Santa Cruz, Calif. A mouse insulin ELISA kit was purchased from DRG (Marburg, Germany) and glucose measurements in both urine and plasma were made using a Boots (Nottingham, UK) glucose kit. L-[U-$^{14}$C] tyrosine (sp.act 16.7 GBqmmol$^{-1}$) was purchased from Perkin Elmer Ltd, (Cambridge, UK), while 2-[1-$^{14}$C] deoxy-D-glucose (sp.act 1.85 GBqmmol$^{-1}$) was from American Radiolabeled Chemicals (Cardiff, UK).

Production and Purification of ZAG—

Figure 3A:
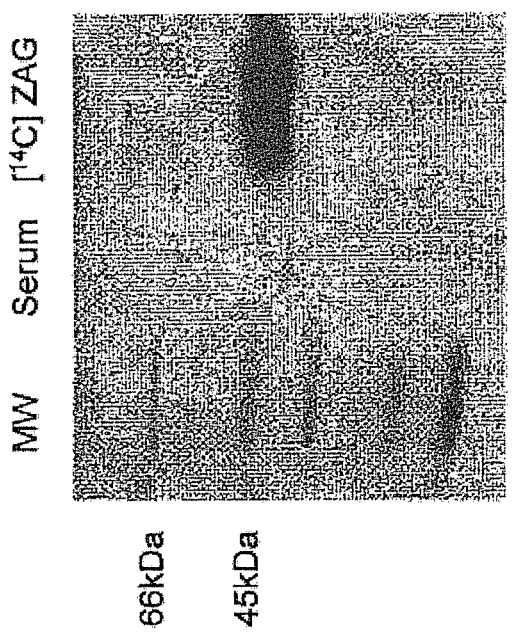
FIG. 3A is a pictorial representation of a SDS/PAGE of purified biosynthetically labelled [$^{14}$C] ZAG (15 μg) and serum from ob/ob mice administered [$^{14}$C] ZAG (50 μg; 212 μCiμmol$^{-1}$) orally for 24 h.

Recombinant human ZAG was produced by HEK293F cells transfected with pcDNA3.1 containing human ZAG (1). Cells were grown for 2 weeks in Freestyle medium containing neomycin (50 μgml$^{-1}$) under an atmosphere of 5% $CO_2$ in air. The cells were then removed by centrifugation (700 g for 15 min), 1 liter of medium was concentrated to 1 ml, and the ZAG was extracted by binding to activated DEAE cellulose, following by elution with 0.3M NaCl before washing and concentrating with sterile PBS. The ZAG produced was greater than 95% pure mainly due to ZAG's negative charge, as determined by sodium dodecyl-sulphate polyacrylamide electrophoresis (SDS PAGE), and was free of endotoxin (1). For [$^{14}$C] ZAG L-[U-$^{14}$C] tyrosine was added to the media (1 μCiml$^{-1}$), the cells were allowed to grow for 2 weeks and ZAG was purified as above. The specific activity of the ZAG was 221 μCiμmol$^{-1}$, and the purity of the product is shown in FIG. 3A.

Cyclic AMP Determination—

CHOK1 cells transfected with human β1-, β2- and β3-AR were maintained in DMEM supplemented with 2 mM glutamine, hygromycin B (50 μgml$^{-1}$), G418 (200 mgml$^{-1}$) and 10% FCS, under an atmosphere of 10% $CO_2$ in air. For cyclic AMP production cells were grown in 24-well plates in 1 ml nutrient medium, and ZAG, after tryptic digestion as described in the legend to FIG. 3C, was incubated for 30 min. The medium was then removed and 0.5 ml of 20 mM HEPES, pH7.5, 5 mM EDTA and 0.1 mM isobutylmethyl-xanthine was added, followed by heating on a water bath for 5 min, and cooling on ice for 10 min. The concentration of cyclic AMP was determined using a Parameter cyclic AMP assay kit (New England Biolabs, Hitchin, Herts, UK).

Animals—

Obese (ob/ob) mice (average weight 65 g) were bred in a colony, and were kept in an air conditioned room at 22+2° C. with ad libitum feeding of a rat and mouse breeding diet (Special Diet Services, Witham, UK) and tap water. These animals exhibit a more severe form of diabetes then C57BL/6J ob/ob mice, and the origins and characteristics of the Aston ob/ob mouse has been previously described. Animals were grouped (n=5) to receive either ZAG/PBS (50 μg day$^{-1}$), or PBS in their drinking water, the experiment was repeated three times after a power analysis was performed. Each mouse consumed 5 ml day$^{-1}$ water, and this did not change on ZAG administration. The ZAG was replaced every 48 h. One group of mice receiving ZAG were also administered propanolol (40 mgkg$^{-1}$, p.o.) daily. The dose of ZAG was chosen to be the same as that previously administered i.v. (1), so that a direct comparison could be made, between the two routes. Body weight, food and water intake, urinary glucose excretion, and body temperature, determined by the use of a rectal thermometer (RS Components, Northants, UK), were measured daily. A glucose tolerance test was performed on day 3. Animals were fasted for 12 h, followed by oral administration of glucose (1 gkg$^{-1}$ in a volume of 100 μl by gavage). Blood samples were removed from the tail vein at 15, 30, 60 and 120 min and used for the measurement of glucose. Urinary glucose was measured by collecting 0.5 ml urine and testing glucose concentration using a Boots glucose monitor. After 8 days of treatment the animals were terminated by cervical dislocation, tissues were removed and rapidly frozen in liquid nitrogen, and maintained at −80° C. Future work would be to repeat this work in diet-induced animals as alternative to a model with gene alteration, although previous studies have shown the ob/ob mouse to be a good indicator of potential human treatments. Animal studies were conducted under Home Office Licence according to the UKCCCR Guidelines for the care and use of laboratory animals.

Glucose Uptake into Adipocytes—

Single cell suspensions of white and brown adipocytes were obtained by incubation of minced epididymal subcutaneous and visceral WAT and BAT for 2 and 2.5 h, respectively, with Krebs-Ringer bicarbonate (KRBB) containing 1.5 mgml$^{-1}$ collagenase and 4% BSA under 95% oxygen-5% $CO_2$ at 37° C. Adipocytes were washed twice in 1 ml KRBB, pH7.2, and then incubated for 10 min at room temperature in 0.5 ml KRBB, containing 18.5 MBq 2-[1-$^{14}$C] deoxy-D-glucose (2-DG), together with non-radioactive 2-DG, to give a final concentration of 0.1 mM, in the absence or presence of insulin (10 nM). Uptake was terminated by addition of 1 ml ice-cold KRBB without glucose. Adipocytes were washed three times with 1 ml KRBB and lysed by the addition of 0.5 ml 1M NaOH. The uptake of 2-[1-$^{14}$C] DG was determined by liquid scintillation counting.

Glucose Uptake into Soleus Muscle—

The uptake of 2-[1-14C] DG into freshly isolated soleus muscles in the absence and presence of insulin (10 nM) was determined as previously described.

Western Blotting Analysis—

Tissues were thawed, washed in PBS and lysed in Phosphosafe™ Extraction reagent for 5 min at room temperature, followed by sonication at 4° C. Cytosolic protein (5-20 ug) formed by centrifugation at 18,000 g for 5 min at 4° C., was resolved on 12% SDS PAGE by electrophoresis at 180V for about 1 h. To determine ZAG in serum 30 μl samples containing 20 μg total protein were electrophoresed as above. Protein was transferred to 0.45 μm nitrocellulose membranes, which had been blocked with 5% (w/v) non-fat dried milk (Marvel) in Tris-buffered saline, pH 7.5, at 4° C. overnight. Membranes were washed for 15 min in 0.1% Tween 20 buffered saline prior to adding the primary antibodies. Both primary and secondary antibodies were used at a dilution of 1:1000. Incubation was for 1 h at room temperature, and development was by ECL. Blots were scanned by a densitometer to quantify differences.

PCR—

Total RNA was extracted from tissues (50-120 mg) and adipocytes with Trizol. RNA samples used for real-time PCR were treated with a DNA-free kit (Ambion) to remove any genomic DNA. The RNA concentration was determined from the absorbance at 260 nM. 1 μg of total RNA of each sample was reverse transcribed to cDNA in a final volume of 20 μl by using a Reverse-iT first strand kit (ABgene). 1 μl of each cDNA sample was then amplified in a PCR mixture containing 0.02 mM of each primer and 1.1•Reddy Mix PCR Master Mix (ABgene) in a final volume of 25 μl. Human b-actin was used as a house keeping gene. The PCR products were sequenced commercially to confirm their identity (MWG Biotech). (7)

RT-PCR—

Relative ZAG mRNA levels were quantified using real-time PCR with an ABI Prism 7700 Sequence Detector (Applied Biosystems). Mouse β-actin mRNA levels were similarly measured and served as the reference gene. Primers and Taqman probes were designed using PrimerExpress software (Applied Biosystems).

Statistical Analysis—

Results are shown as mean±SEM for at least three replicate experiments. Differences in means between groups were determined by one-way analysis of variance (ANOVA) followed by Tukey-Kramer multiple comparison tests, p values <0.05 were considered significant.

Figure 1B:
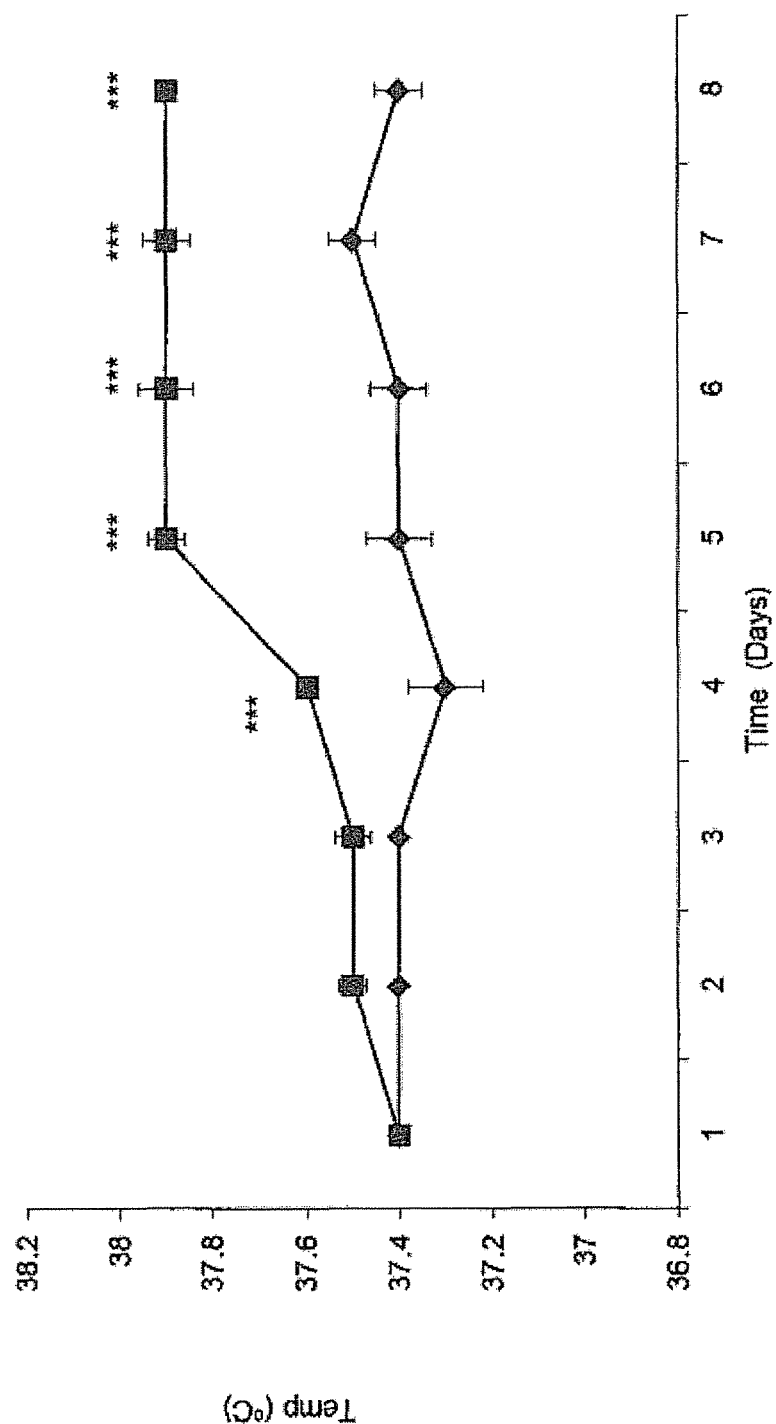
Figure 1C:
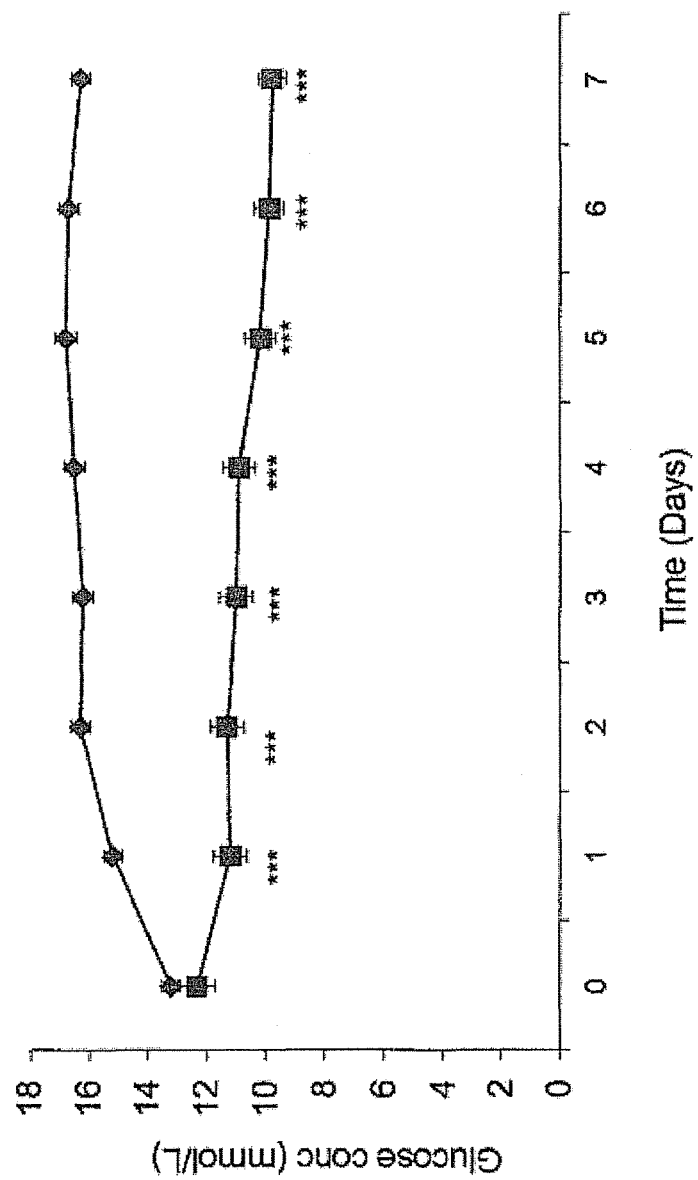
Figure 2A:
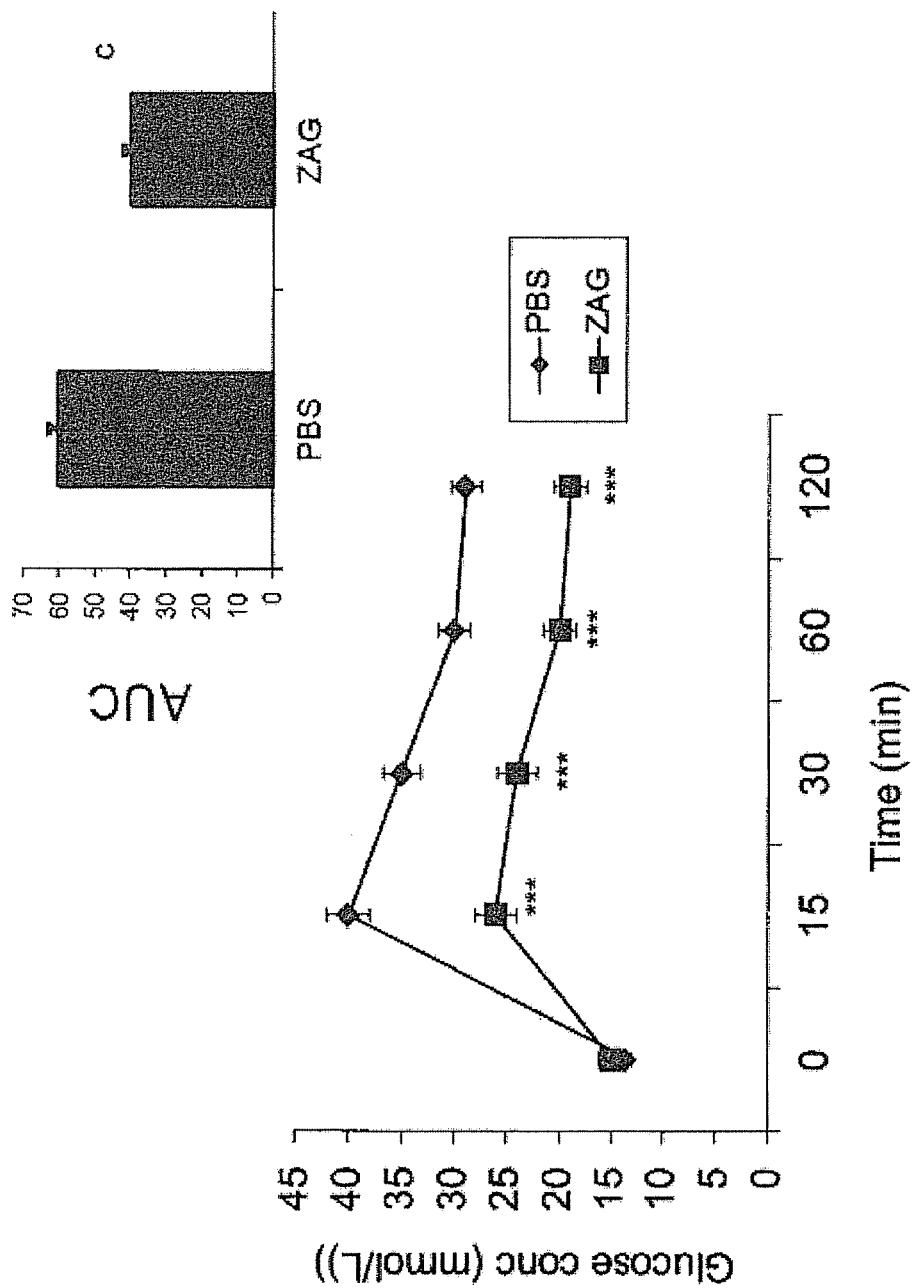
FIGS. 2A-2G are graphical diagrams showing the effect of orally administered human ZAG (■) compared with PBS (♦) on glucose and insulin tolerance of ob/ob mice after 3 days of treatment. Animals were fasted for 12 h before oral administration of glucose (1 gkg$^{-1}$ in a volume of 100 μl). Blood samples were removed from the tail vein at the time intervals shown and used for the measurement of serum glucose (FIG. 2A) and insulin (FIG. 2B). The inset in (FIG. 2A) shows the total area under the glucose curves (AUC) in arbitrary units. Differences from PBS controls are shown as *, p<0.001. Effect of propranolol (40 mgkg$^{-1}$, po, daily) on ZAG-induced reductions in obesity and diabetes in ob/ob mice. Animals received ZAG (50 μg daily) in their drinking water as described in the legend to FIG. 1, either alone (■) or in the presence of propranolol (▲), while a control group received PBS (♦). Changes in body weight (FIG. 2C), rectal temperature (FIG. 2D), and urinary glucose excretion (FIG. 2E) were monitored over a 8 day period. A glucose tolerance test (FIG. 2F), with measurement of serum insulin levels (FIG. 2G) was made 3 days after starting the oral ZAG. Differences from PBS controls are shown as *, p<0.001, while differences from ZAG alone are shown as #, p<0.001.
Figure 2B:
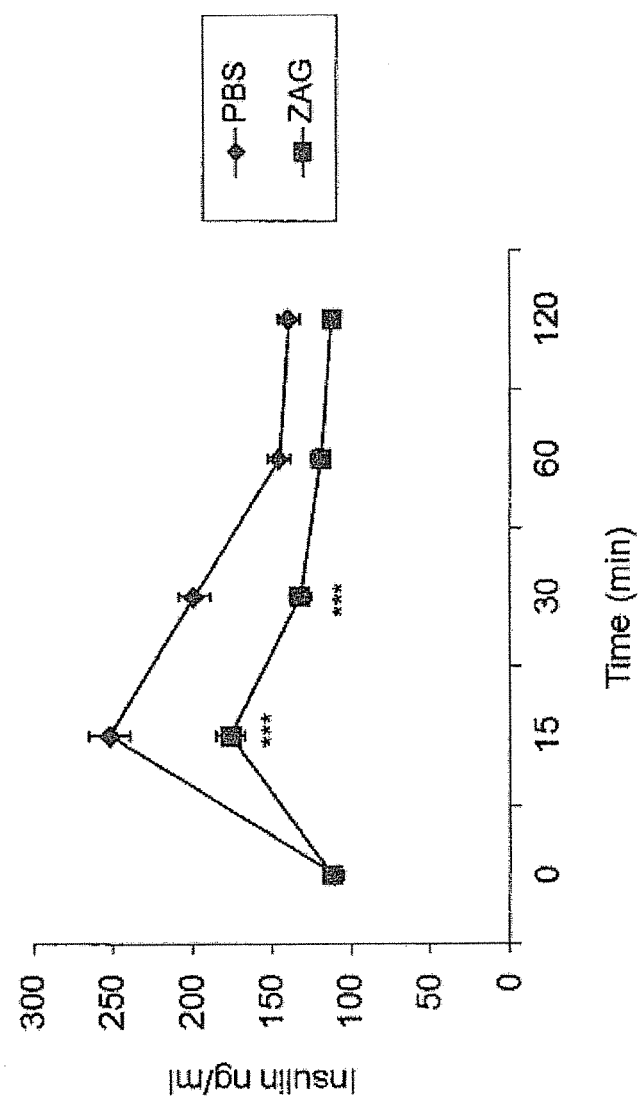
Figure 2C:
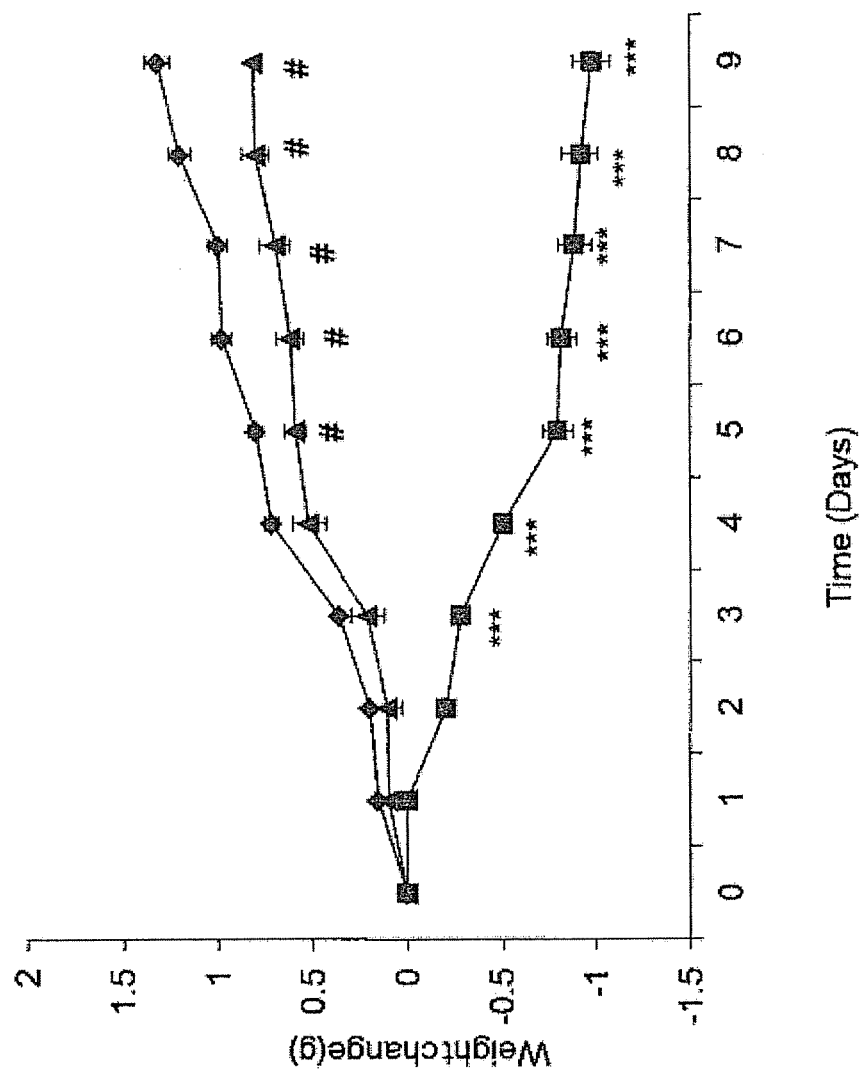
Figure 2D:
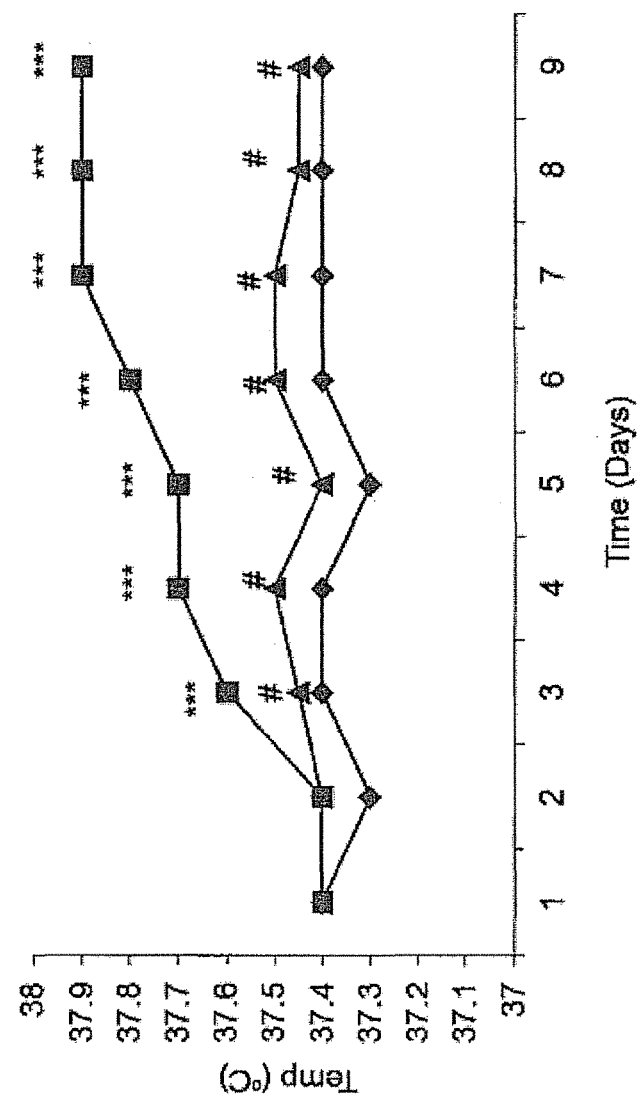
Figure 2E:
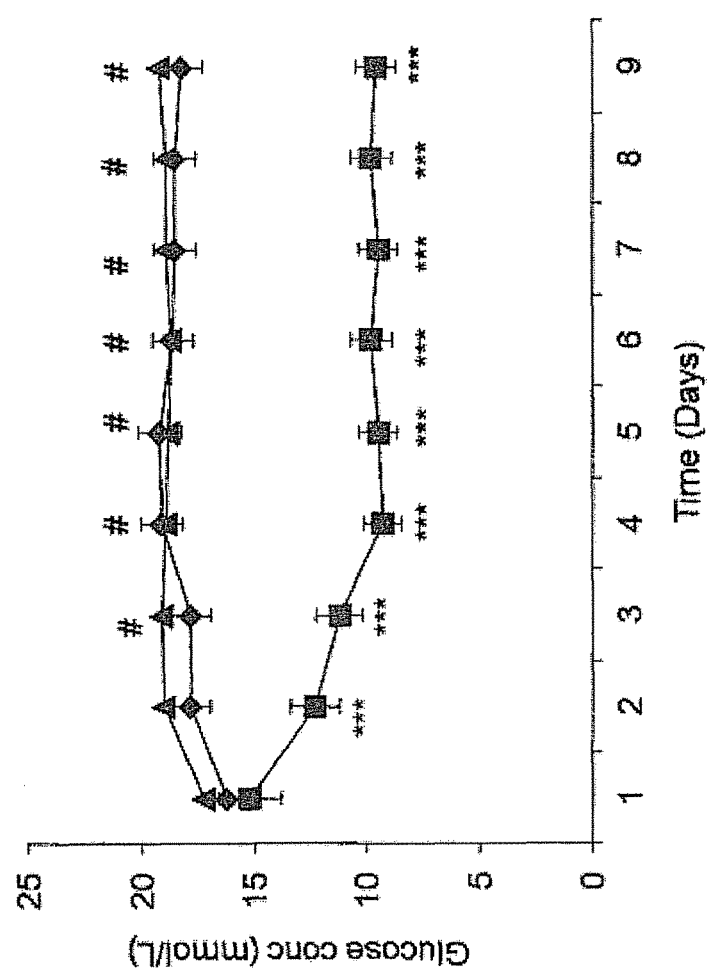
Figure 2F:
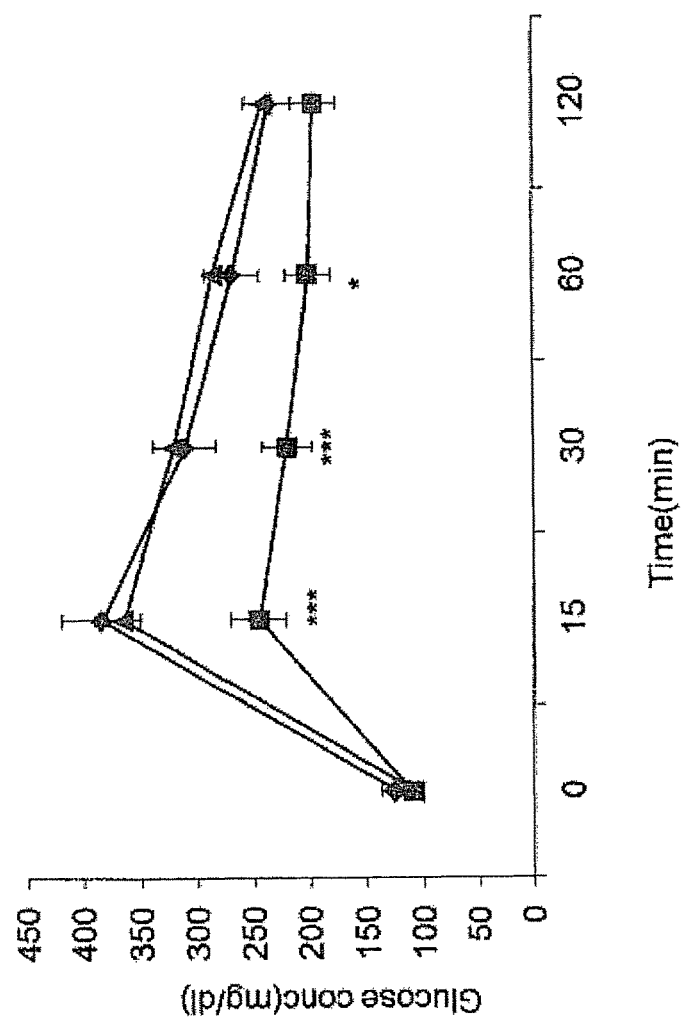
Figure 2G:
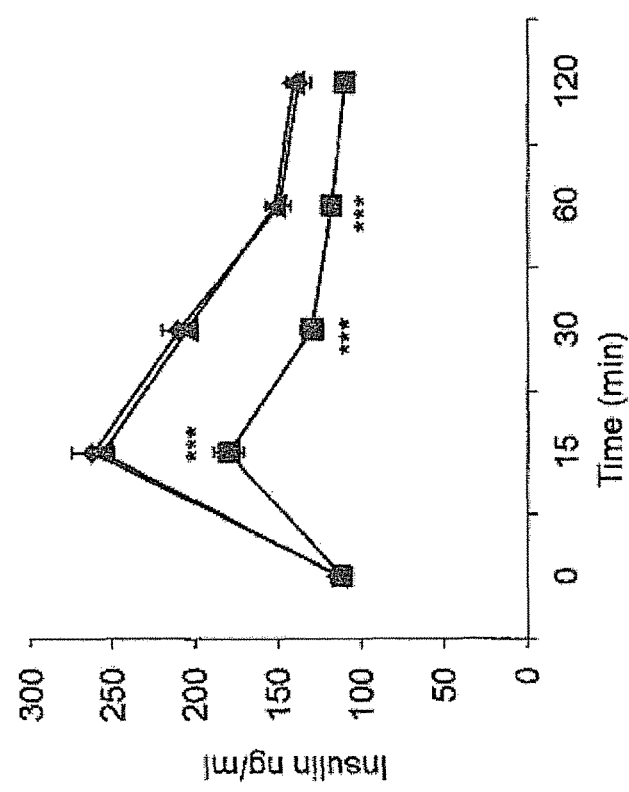

Previous studies have shown that animals treated with iv ZAG consume the same amount of food and water as PBS controls. It was therefore convenient for oral administration to dissolve the ZAG in drinking water, since this would avoid the stress associated with dosing by gavage. The concentration of ZAG in the drinking water was such that the animals would consume 50 μg per day, so that a direct comparison could be made with the iv route. The effect of oral ZAG on the body weight of ob/ob mice is shown in FIG. 1A. After 5 days of treatment the difference in body weight between the ZAG and PBS groups was 3.5 g, which was the same as that found after i.v. administration, while after 8 days of treatment there was 5 g weight difference between the groups. As with i.v. administration of ZAG there was an increase in rectal temperature, which became significant after 4 days of treatment (FIG. 1B), while there was a 40% reduction in urinary glucose excretion, which became significant after 1 day of treatment (FIG. 1C). This suggests that the oral ZAG also reduced the severity of diabetes in the ob/ob mouse. A glucose tolerance test, performed on animals after 3 days of oral ZAG, showed a reduced peak blood glucose concentration, and a 33% reduction in the total area under the curve (AUC) during the entire glucose tolerance test in ZAG treated animals (FIG. 2A). ZAG also decreased the insulin response to the glucose challenge (FIG. 2B) although a direct comparison has not been made. These results suggest that oral administration of ZAG is as effective in inducing weight loss, and reducing the severity of diabetes in ob/ob mice as when given by the i.v. route. To determine whether this effect was due to interaction with a β-AR, ZAG was administered orally to ob/ob mice that were co-administered the non-specific β-AR antagonist propanolol (40 mg/kg). As shown in FIG. 2C while mice administered ZAG orally lost weight this was blocked with propanolol, which had no effect on weight gain of mice, administered PBS. Initially propanolol was administered at 20 mgkg$^{-1}$, but this did not prevent the weight loss with ZAG so the dose was increased to 40 mgkg$^{-1}$ Antagonists of β1- and β2-AR are known to be less effective against β3-AR responses. Propanolol also completely attenuated the ZAG induced increase in rectal temperature (FIG. 2D) and the reduction in urinary excretion of glucose (FIG. 2E). Propanolol also blocked the reduced peak blood glucose concentration in the glucose tolerance test (FIG. 2F) and the increase in insulin sensitivity (FIG. 2G). Propanolol also completely attenuated the decrease in serum glucose and insulin levels after ZAG administration to ob/ob mice. The elevation of serum glycerol level, suggesting that it blocked lipolysis induced by ZAG, along with the decrease in serum triglycerides and non-esterified fatty acids (Table 1).

Figure 3B:
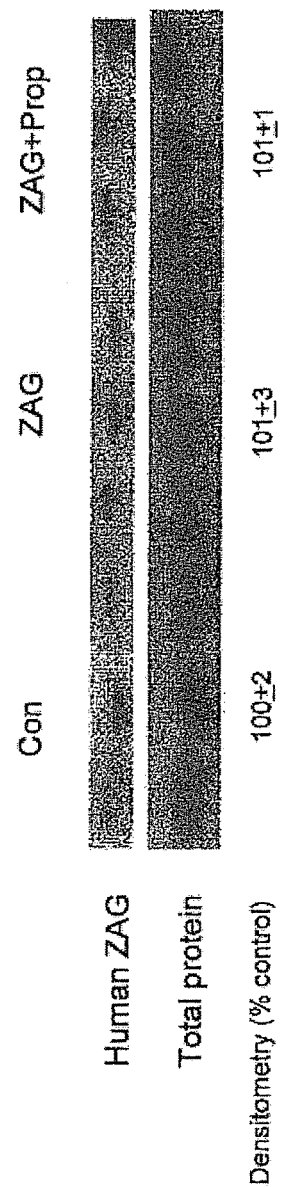
FIG. 3B is a pictorial representation of a western blot of serum from ob/ob mice administered non-radioactive ZAG for 8 days in the absence or presence of propanolol (40 mg kg$^{-1}$) using anti-human ZAG monoclonal antibody.
Figure 3C:
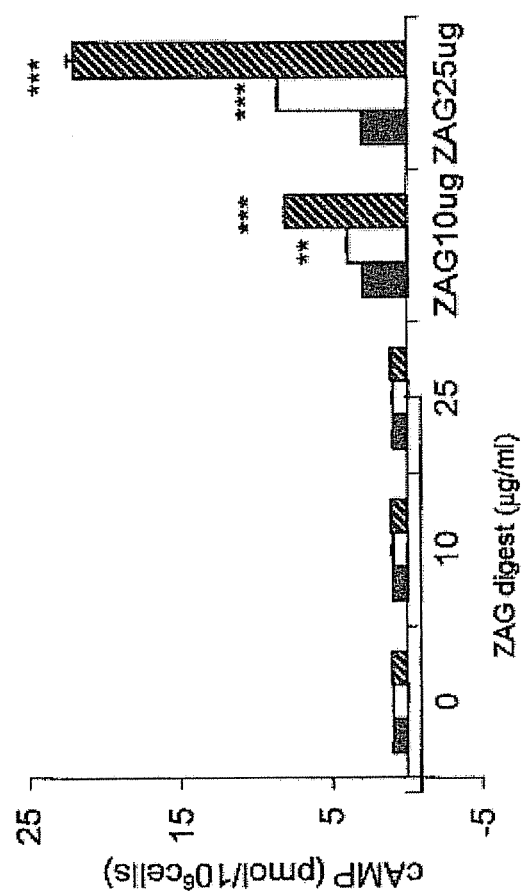
FIG. 3C is a graphical representation of the effect of a tryptic digest of ZAG in comparison with intact ZAG on cyclic AMP production by CHO cells transfected with human β1-AR (■), β2-AR(□) and β3-AR) (▨) after 30 min incubation. ZAG (1 mg) was incubated with trypsin (200 μg) in 1 ml 10 mM Tris.HCl, pH8 for 4 h at 37° C. and proteolysis was terminated by addition of the trypsin inhibitor (200 μg). High molecular weight material was removed by a Sephadex G25 column followed by dialysis using an Amicon filtration cell containing a 10 kDa cut-off membrane filter.

One possibility by which this could occur is that ZAG escapes digestion by proteolytic enzymes, and is absorbed directly into the blood stream. To investigate this ZAG was biosynthetically labelled with L-[U-$^{14}$C] tyrosine. SDS/PAGE showed that the purified product contained a single band of radioactivity of Mr43kDa (FIG. 3A). The [$^{14}$C]ZAG was then administered to ob/ob mice by the oral route. SDS PAGE of serum proteins provided no evidence for intact ZAG (FIG. 3A). Western blotting of serum using mouse monoclonal antibody to full-length human ZAG, confirmed the absence of human ZAG (FIG. 3B). Another possibility is that a tryptic digest of ZAG could mediate the effect, but there is no evidence for absorption of peptides into the blood stream (FIG. 3A). Alternatively a peptide could act within the gastrointestinal tract. The effect of ZAG has been shown to be manifested through interaction with a β3-AR. However, treatment of CHO cells transfected with human β1-, β2 or β3-AR with a tryptic digest of ZAG had no effect on cyclic AMP production (FIG. 3C), while intact ZAG stimulated cyclic AMP production in cells with β2- and β3-AR. This suggests that interaction with trypsin in the stomach would inactivate ZAG. Therefore ZAG must act before it reaches the stomach.

Figure 4A:
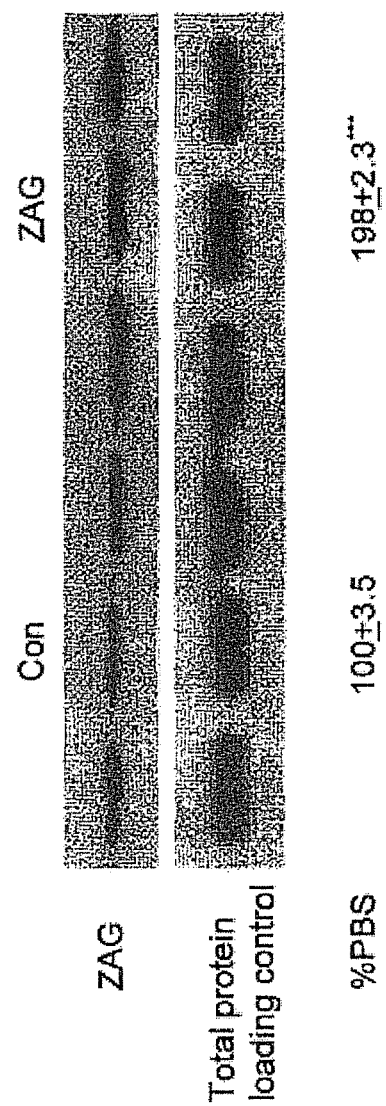
FIGS. 4A-4C are a series of pictorial representation of a western blots of ZAG.
Figure 4B:
Figure 4C:
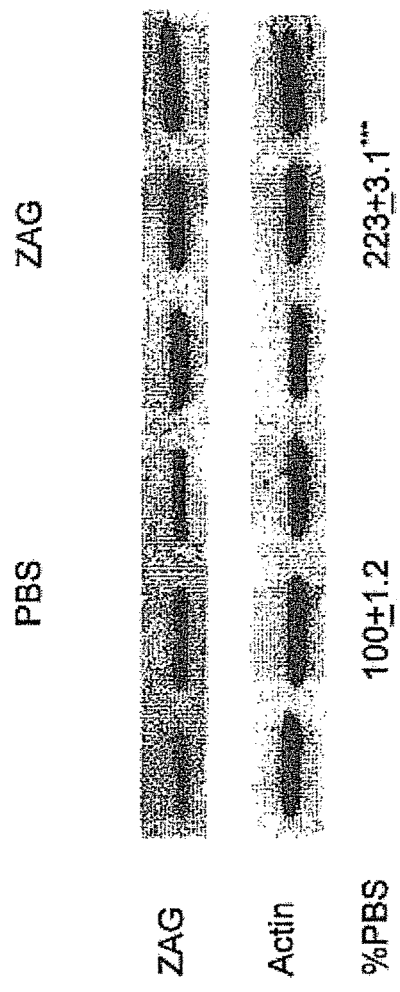
Figure 5A:
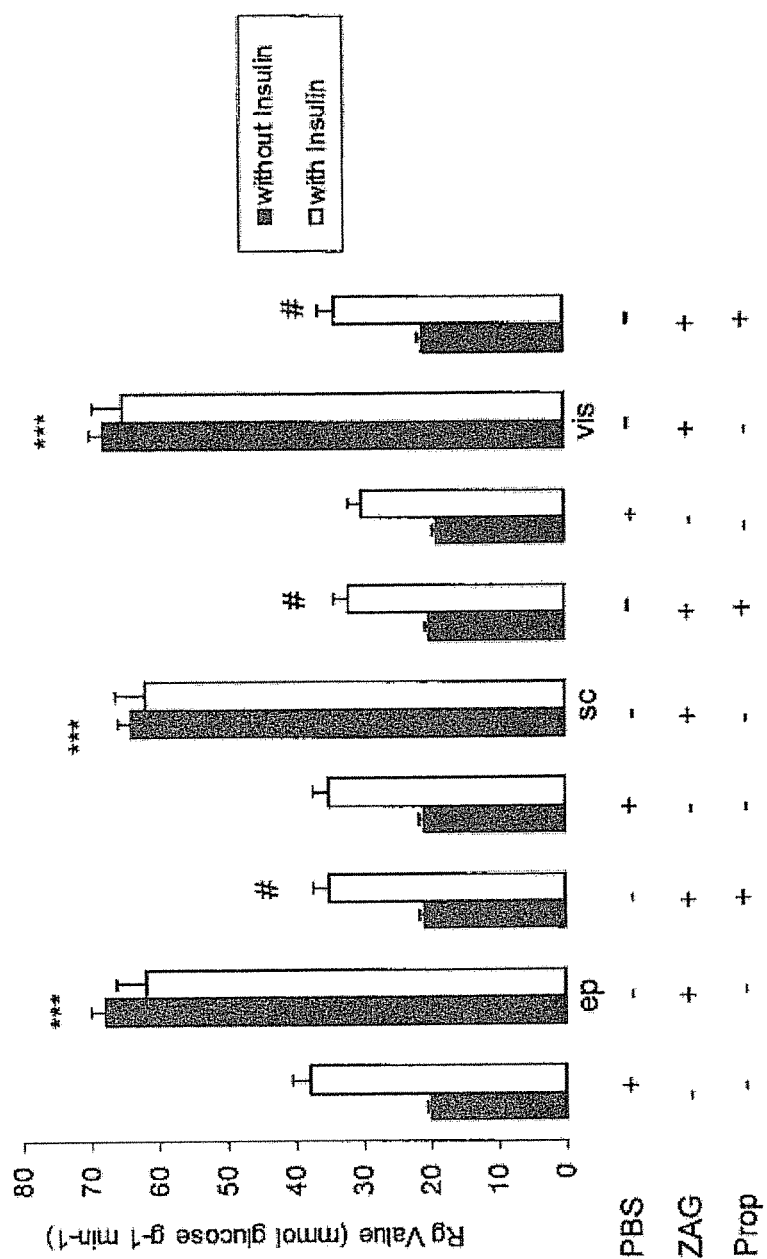
FIGS. 5A-5D are a series of graphical and pictorial representations showing the effect of propanolol on the stimulation of glucose uptake into WAT, BAT and skeletal muscle of ob/ob mice ex vivo after administration of ZAG.
Figure 5B:
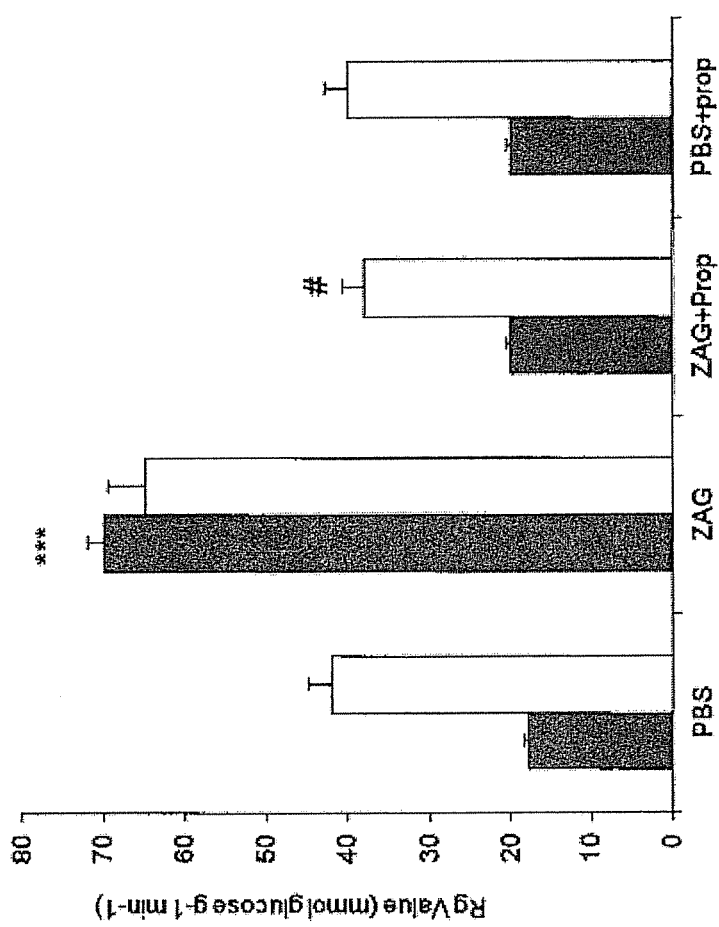
Figure 5C:
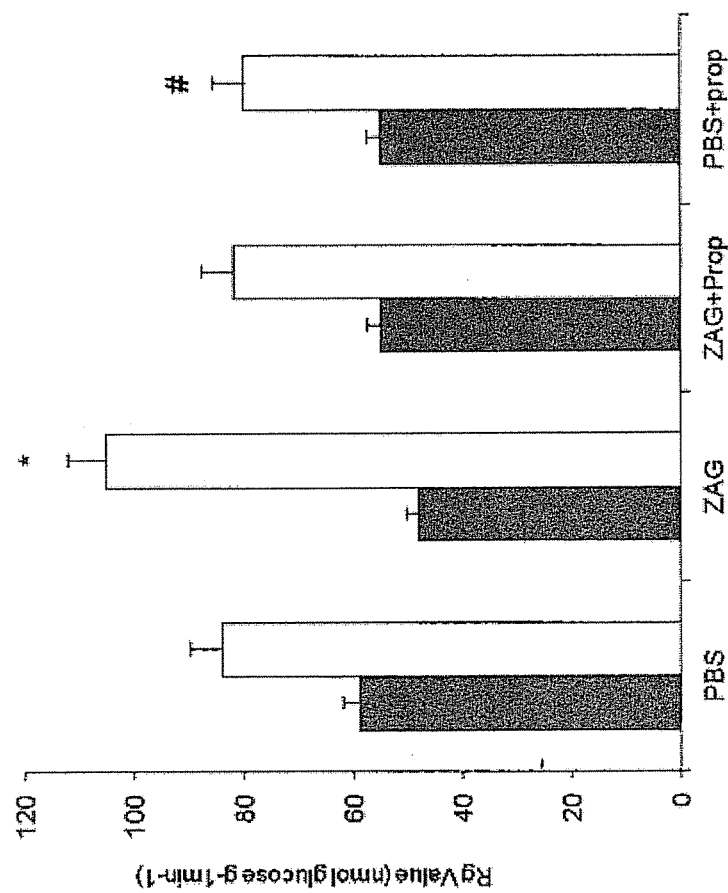
Figure 5D:
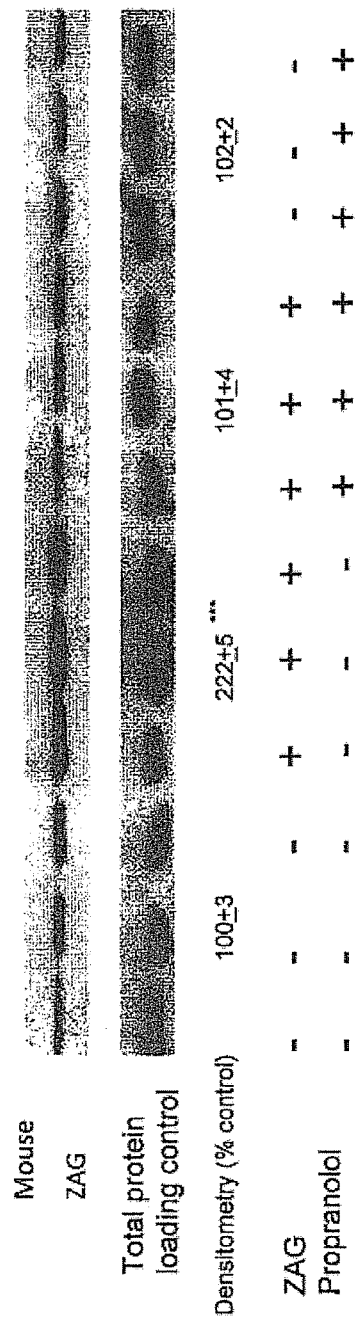
Figure 6C:
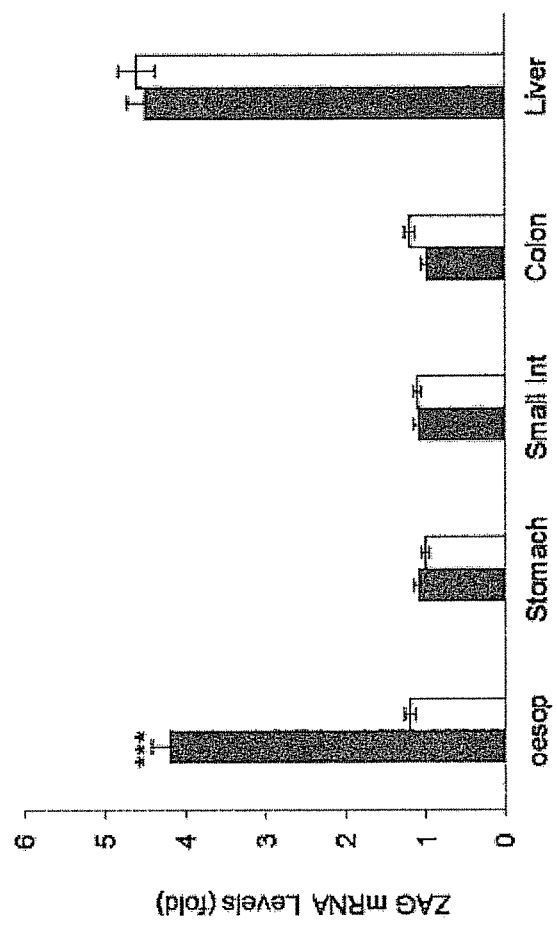

Previous studies have shown that ZAG can induce its own expression through interaction with a β3-AR. and may be able to induce its own expression through interaction with β3-AR in the oesophagus before being digested in the stomach and other parts of the gastrointestinal tract. Since there was an absence of human ZAG in the serum of orally dosed mice (FIG. 3B). Western blotting of serum from mice dosed orally with ZAG for 8 days showed a two-fold (P<0.001) increased level of murine ZAG (FIG. 4A). The specificity of the antibodies against human ZAG is shown in FIG. 4B. Thus the anti-mouse ZAG antibody did not detect human ZAG. Therefore the human ZAG administered orally has resulted in an increase in mouse ZAG in the serum, and this has also caused a two fold rise of mouse ZAG in WAT (P<0.001) (FIG. 4C). Administration of propanolol also attenuated the oral route ZAG-induced stimulation of glucose uptake ex vivo into epididymal, subcutaneous and visceral adipocytes in the absence and presence of insulin (FIG. 5A), It also attenuated glucose uptake into BAT in the absence and presence of insulin (FIG. 5B), and glucose uptake ex vivo into gastrocnemius muscle in the presence of insulin (FIG. 5C). In addition there was no increase in murine ZAG in the serum (FIG. 5D), and no evidence of human ZAG (FIG. 3B) in animals co-administered propanolol. These results suggest that oral administration of ZAG increases circulatory levels by interaction with a β-AR, probably in the oesophagus, since ZAG mRNA appears to be dramatically increased in oesophageal tissue compared to that of the stomach, small intestine or the colon and is on par with that seen in the liver in mice treated with ZAG orally (FIGS. 6A and B). Gene expression for ZAG in the various sections of the GI Track are shown in (FIG. 6C).

Previous studies have shown ZAG to bind to a high affinity binding site on the β3-AR, with a Kd value of 78±45 nM and Bmax of 282±1 fmole mg protein$^{-1}$. Many of the effects of ZAG are also found with β3-AR agonists, including an increased lipid mobilization and reduction of body fat, an increase of rectal temperature and induction of UCP1 in BAT, normalization of hyperglycaemia and hyper insulinaemia, improvement in glucose tolerance and reduction of the insulin response during a glucose tolerance test, and also attenuation of muscle wasting. The β3-AR is found predominantly on adipocytes, but has also been reported on BAT and prostate as well as in the smooth muscle of the gastrointestinal tract in a variety of species, and mediates relaxation in the ileum, gastric fundus, jejunum, colon and oesophagus. This study has shown that the previously described presence of a β-AR in the gastrointestinal tract, coupled with the ability of ZAG to induce its own expression through a β-AR enables ZAG to be administered orally and this stimulus to be converted into circulating ZAG.

The β-AR responsive to oral ZAG must be in the mouth or oesophagus, since tryptic digestion of ZAG produced a product with no stimulation of the β-AR. Using RT-PCR analysis of ZAG mRNA this study shows a large increase in the oephagus of animals receiving ZAG orally. The lack of expression of ZAG in the lower part of the gastrointestinal tract, despite the reported presence of β-AR would support the contention that ZAG is digested in the stomach. Previous studies have suggested that a tryptic digest of a cancer lipolytic factor called toxohormone L still retains biological activity. The mechanism by which the ZAG signal is transmitted from the gastrointestinal tract to the general circulation has been elucidated by administration of human ZAG to a mouse, and depends on the specificities of the antibodies to human and murine ZAG. As expected human ZAG is digested, but murine ZAG appears in the serum and responsive tissue such as WAT. This effect is mediated through a β-AR, since mice treated with the non-specific β-AR antagonist, propanolol, showed no murine ZAG in their serum, and the effects of ZAG on body weight, lipolysis and glucose disposal were completely attenuated. Previous studies have shown that the lipolytic effect of ZAG in vitro was also completely attenuated by propanolol. Agents that have been reported to be specific for β3-AR, such as SR59230A, were note used since previous studies have indicated that this antagonist also attenuates activation through both the β1 and β2-AR while other investigators have shown it to be an antagonist of the α1-AR). SR59230A has also been seen to bind to albumin when used in vivo. The specific β-AR involved can only be determined using specific β-AR "knock-out" animals. The ability of propanolol to attenuate the reduction in body weight, increase in temperature, reduction in blood glucose, insulin, NEFA, and triglycerides, increase in serum glucose, disposal of glucose and increased insulin sensitivity induced by ZAG in ob/ob mice suggests that these effects are mediated through a β-AR.

The effects of orally administered human ZAG at a dose of 50 µg day$^{-1}$ are almost identical to those found when human ZAG was administered by the i.v. route, suggesting a quantitative transfer of the message from human ZAG into the serum as mouse ZAG. ZAG is unusual in inducing its own expression, and the mechanism is unknown apart from a requirement of the β3-AR. The β3-AR agonist BRL37344 has also been shown to increase levels of ZAG mRNA in 3T3 L1 adipocytes, suggesting a common mechanism. The cyclic AMP faulted from interaction with a β3-AR would lead to activation of protein kinase A (PKA), the C-subunits of which are capable of passively diffusing into nucleus, where they can regulate gene expression through direct phosphorylation of cyclic AMP response element binding protein (CREB).

Plasma ZAG protein has been shown to be decreased in ob/ob mice and a similar decrease has been reported in high fat diet-fed mice. Serum ZAG levels have also been found to be low in obese human subjects. Most of the serum ZAG is thought to come from adipose tissue and liver, and expression levels of ZAG mRNA in these tissues in ob/ob mice have been shown to be significantly reduced. This is at least partly due to the pro-inflammatory cytokine tumour necrosis factor-α (TNF-α), which is elevated in adipose tissue of obese subjects. Many of the effects of obesity may be due to this low expression of ZAG, because of its function in regulating lipid metabolism, and ZAG's ability to increase expression of β3-AR in gastrocnemius muscle, BAT and WAT (unpublished results), which are low in obesity. The ability of ZAG to increase serum levels when administered by the oral route provides a mechanism for countering some of the effects of obesity. It also raises the possibility of some uncooked foods such as broccoli, rich in ZAG functioning to control obesity and type 2 diabetes, through conversion of vegetable ZAG to human ZAG.

Although the invention has been described with reference to the above example, it will be understood that modifications and variations are encompassed within the spirit and scope of the invention. Accordingly, the invention is limited only by the following claims.

What is claimed is:

1. A method for increasing a mammal's endogenous expression of a zinc-α$_2$-glycoprotein (ZAG) comprising contacting the oesophagus of the mammal with a formulation comprising an exogenous zinc-α$_2$-glycoprotein (ZAG), wherein upregulated production of endogenous ZAG in the subject is detectable by obtaining one or more tissue or fluid samples from the subject and detecting an increase in the level of endogenous ZAG in the sample and an absence of a therapeutically effective level of exogenous ZAG in the sample, thereby increasing the mammal's endogenous expression of ZAG as compared to the mammal's expression of ZAG prior to contacting.

2. The method of claim 1, wherein the exogenous ZAG is administered to the oesophagus via oral, buccal, sublingual, intranasal delivery routes, or other delivery routes that contact the oesophagus.

3. The method of claim 1, wherein the mammal has one or more symptoms associated with diabetes, lipidystrophy, obesity or overweight, including diseases associated with insulin resistance, hypoglycemia, elevated plasma levels of free fatty acids (NEFA), triglycerides, or glucose, or has a need to reduce fat levels, reduce glucose levels, or increase ZAG levels.

4. The method of claim 1, wherein the ZAG is mammalian.

5. The method of claim 4, wherein the exogenous ZAG is human.

6. The method of claim 1, wherein the mammal is human.

7. The method of claim 5, wherein the exogenous ZAG consists of the amino acid sequence set forth in SEQ ID NO: 1.

8. The method of claim 4, wherein the exogenous ZAG is conjugated to a non-protein polymer comprising sialylated, pegylated, or is modified to increase solubility or stability.

9. The method of claim 1, wherein the exogenous ZAG is administered in combination with a glycemic reducing agent.

10. The method of claim 1, wherein the exogenous ZAG is formulated with one or more of the following: micronutrients, dietary supplements, nutrients, edible compounds and flavorings, excipients selected from the group consisting of phosphate, Tris, arginine, glycine, Tween 80, sucrose, trehalose, mannitol, casein proteins, and derivatives thereof.

11. The method of claim 1, wherein the exogenous ZAG is administered in combination with one or more β3 agonists in any sequence or simultaneously.

12. The method of claim 11, wherein the β3 agonist is selected from the group consisting of epinephrine (adrenaline), norepinephrine (noradrenaline), isoprotenerol, isoprenaline, propranolol, alprenolol, arotinolol, bucindolol, carazolol, carteolol, clenbuterol, denopamine, fenoterol, nadolol, octopamine, oxyprenolol, pindolol, [(cyano)pindolol], salbuterol, salmeterol, teratolol, tecradine, trimetoquinolol, 3'-iodotrimetoquinolol, 3',5'-iodotrimetoquinolol, Amibegron, Solabegron, Nebivolol, AD-9677, AJ-9677, AZ-002, CGP-12177, CL-316243, CL-317413, BRL-37344, BRL-35135, BRL-26830, BRL-28410, BRL-33725, BRL-37344, BRL-35113, BMS-194449, BMS-196085, BMS-201620, BMS-210285, BMS-187257, BMS-187413, the CONH2 substitution of SO3H of BMS-187413, the racemates of BMS-181413, CGP-20712A, CGP-12177, CP-114271, CP-331679, CP-331684, CP-209129, FR-165914, FR-149175, ICI-118551, ICI-201651, ICI-198157, ICI-D7114, LY-377604, LY-368842, KTO-7924, LY-362884, LY-750355, LY-749372, LY-79771, LY-104119, L-771047, L-755507, L-749372, L-750355, L-760087, L-766892, L-746646, L-757793, L-770644, L-760081, L-796568, L-748328, L-748337, Ro-16-8714, Ro-40-2148, (−)-RO-363, SB-215691, SB-220648, SB-226552, SB-229432, SB-251023, SB-236923, SB-246982, SR-58894A, SR-58611, SR-58878, SR-59062, SM-11044, SM-350300, ZD-7114, ZD-2079, ZD-9969, ZM-215001, and ZM-215967.

13. The method of claim 1, wherein the levels of glucose and fat decrease as compared to the glucose and fat levels prior to the step of contacting.

14. The method of claim 1, wherein the one or more tissue or fluid samples are selected from the group consisting of blood, plasma, adipose tissue, WAT, BAT, liver, and skeletal muscle.

* * * * *

SEQUENCE LISTING

<160> NUMBER OF SEQ ID NOS: 1

<210> SEQ ID NO 1
<211> LENGTH: 276
<212> TYPE: PRT
<213> ORGANISM: Homo sapiens

<400> SEQUENCE: 1

Gln Glu Asn Gln Asp Gly Arg Tyr Ser Leu Thr Tyr Ile Tyr Thr Gly
1               5                   10                  15

Leu Ser Lys His Val Glu Asp Val Pro Ala Phe Gln Ala Leu Gly Ser
            20                  25                  30

Leu Asn Asp Leu Gln Phe Phe Arg Tyr Asn Ser Lys Asp Arg Lys Ser
        35                  40                  45

Gln Pro Met Gly Leu Trp Arg Gln Val Glu Gly Met Glu Asp Trp Lys
    50                  55                  60

Glu Asp Ser Gln Leu Gln Lys Ala Arg Glu Asp Met Glu Thr Leu Lys
65                  70                  75                  80

Asp Ile Val Glu Tyr Tyr Asn Asp Ser Asn Gly Ser His Val Leu Gln
                85                  90                  95

Gly Arg Phe Gly Cys Glu Ile Glu Asn Asn Arg Ser Ser Gly Ala Phe
            100                 105                 110

-continued

```
Trp Lys Tyr Tyr Tyr Asp Gly Lys Asp Tyr Ile Glu Phe Asn Lys Glu
        115                 120                 125

Ile Pro Ala Trp Val Pro Phe Asp Pro Ala Ala Gln Ile Thr Lys Gln
    130                 135                 140

Lys Trp Glu Ala Glu Pro Val Tyr Val Gln Arg Ala Lys Ala Tyr Leu
145                 150                 155                 160

Glu Glu Glu Cys Pro Ala Thr Leu Arg Lys Tyr Leu Lys Tyr Ser Lys
                165                 170                 175

Asn Ile Leu Asp Arg Gln Asp Pro Pro Ser Val Val Val Thr Ser His
            180                 185                 190

Gln Ala Pro Gly Glu Lys Lys Lys Leu Lys Cys Leu Ala Tyr Asp Phe
        195                 200                 205

Tyr Pro Gly Lys Ile Asp Val His Trp Thr Arg Ala Gly Gln Val Gln
    210                 215                 220

Glu Pro Glu Leu Arg Gly Asp Val Leu His Asn Gly Asn Gly Thr Tyr
225                 230                 235                 240

Gln Ser Trp Val Val Val Ala Val Pro Pro Gln Asp Thr Ala Pro Tyr
                245                 250                 255

Ser Cys His Val Gln His Ser Ser Leu Ala Gln Pro Leu Val Val Pro
            260                 265                 270

Trp Glu Ala Ser
        275
```